(12) United States Patent
Hickey et al.

(10) Patent No.: US 7,377,277 B2
(45) Date of Patent: May 27, 2008

(54) BLISTER PACKAGES WITH FRAMES AND ASSOCIATED METHODS OF FABRICATING DRY POWDER DRUG CONTAINMENT SYSTEMS

(75) Inventors: Anthony James Hickey, Chapel Hill, NC (US); Timothy Crowder, Durham, NC (US); Jeffrey Alan Warden, Raleigh, NC (US); Keith Arthur Johnson, Durham, NC (US); Mark Ennis Ketner, Apex, NC (US); Jay Kinsley Fording, Matthews, NC (US); Michael Duane Garten, Charlotte, NC (US); William Myles Riley, Richmond, VA (US); Sean Derek Anderson, Richmond, VA (US); Bruce Seymour Ferris, Richmond, VA (US); Paul Gilbert Rockwell, Chesterfield, VA (US)

(73) Assignee: Oriel Therapeutics, Inc., Durham, NC (US)

( * ) Notice: Subject to any disclaimer, the term of this patent is extended or adjusted under 35 U.S.C. 154(b) by 587 days.

(21) Appl. No.: 10/970,549

(22) Filed: Oct. 21, 2004

(65) Prior Publication Data
US 2005/0109659 A1  May 26, 2005

Related U.S. Application Data

(60) Provisional application No. 60/514,727, filed on Oct. 27, 2003.

(51) Int. Cl.
*A61M 15/00* (2006.01)
*A61M 16/00* (2006.01)
*B05D 7/14* (2006.01)
*B65D 83/06* (2006.01)

(52) U.S. Cl. ............... 128/203.21; 128/203.15; 128/203.19

(58) Field of Classification Search ........... 128/203.21, 128/230.15, 230.19; 206/528, 530–532, 206/538–539
See application file for complete search history.

(56) References Cited

U.S. PATENT DOCUMENTS

| 3,565,070 A | 2/1971 | Hanson et al. |
| 3,812,854 A | 5/1974 | Michaels et al. |
| 3,948,264 A | 4/1976 | Wilke et al. ........... 128/203.15 |
| 3,948,284 A | 4/1976 | Walworth |
| 3,962,917 A | 6/1976 | Terada |
| 3,971,377 A | 7/1976 | Damani |

(Continued)

FOREIGN PATENT DOCUMENTS

EP          0129985          1/1985

(Continued)

OTHER PUBLICATIONS

U.S. Appl. No. 11/052,627, Warden.

(Continued)

*Primary Examiner*—Justine R. Yu
*Assistant Examiner*—Kristen C Matter
(74) *Attorney, Agent, or Firm*—Myers Bigel Sibley & Sajovec

(57) ABSTRACT

Dry powder blister packages include sealed blisters with a piezoelectric active layer that flexes to vibrate the dry powder in a blister to facilitate active dispersion.

**55 Cla

U.S. PATENT DOCUMENTS

| | | | |
|---|---|---|---|
| 3,989,042 A | 11/1976 | Mitsui et al. | |
| 4,113,809 A | 9/1978 | Abair et al. | |
| 4,147,166 A | 4/1979 | Hansen | |
| 4,319,155 A | 3/1982 | Nakai et al. | 310/316 |
| 4,393,884 A | 7/1983 | Jacobs | |
| 4,446,862 A | 5/1984 | Baum et al. | |
| 4,472,091 A | 9/1984 | Callahan | 406/132 |
| 4,537,312 A * | 8/1985 | Intini | 206/531 |
| 4,600,855 A | 7/1986 | Strachan | |
| 4,607,254 A | 8/1986 | Carlson | |
| 4,648,393 A | 3/1987 | Landis et al. | |
| 4,778,054 A | 10/1988 | Newell et al. | 206/531 |
| 4,819,629 A | 4/1989 | Jonson | |
| 4,877,989 A | 10/1989 | Drews et al. | |
| 5,063,922 A | 11/1991 | Hakkinen | |
| 5,207,217 A * | 5/1993 | Cocozza et al. | 128/203.21 |
| 5,349,947 A | 9/1994 | Newhouse et al. | 128/203.21 |
| 5,363,842 A | 11/1994 | Mishelevich et al. | |
| 5,388,572 A | 2/1995 | Mulhauser et al. | 128/203.15 |
| 5,437,271 A | 8/1995 | Hodson et al. | 128/203.15 |
| 5,469,843 A | 11/1995 | Hodson | 128/203.15 |
| 5,482,030 A | 1/1996 | Klein | 128/200.23 |
| 5,482,032 A | 1/1996 | Smith et al. | 128/203.15 |
| 5,497,764 A | 3/1996 | Ritson et al. | 128/200.14 |
| 5,505,196 A | 4/1996 | Herold et al. | 128/203.15 |
| 5,507,277 A | 4/1996 | Rubsamen et al. | 128/200.14 |
| 5,509,404 A | 4/1996 | Lloyd et al. | 128/200.14 |
| 5,520,166 A | 5/1996 | Ritson et al. | 128/200.14 |
| 5,522,378 A | 6/1996 | Ritson et al. | 128/200.14 |
| 5,522,385 A | 6/1996 | Lloyd et al. | 128/203.26 |
| 5,533,502 A | 7/1996 | Piper | 128/203.21 |
| 5,542,410 A | 8/1996 | Goodman et al. | 128/200.14 |
| 5,544,646 A | 8/1996 | Lloyd et al. | 128/200.14 |
| 5,558,085 A | 9/1996 | Rubsamen et al. | 128/200.14 |
| 5,577,497 A | 11/1996 | Mecikalski et al. | 128/203.15 |
| 5,608,647 A | 3/1997 | Rubsamen et al. | 364/509 |
| 5,618,177 A | 4/1997 | Abbott | 433/88 |
| 5,619,984 A | 4/1997 | Hodson et al. | 128/203.15 |
| 5,622,162 A | 4/1997 | Eisele et al. | 128/203.12 |
| 5,622,166 A | 4/1997 | Cameron et al. | 128/203.12 |
| 5,642,727 A | 7/1997 | Datta et al. | 128/203.15 |
| 5,655,523 A | 8/1997 | Hodson et al. | 128/203.15 |
| 5,660,166 A * | 8/1997 | Lloyd et al. | 128/200.14 |
| 5,672,581 A | 9/1997 | Rubsamen et al. | 514/3 |
| 5,694,919 A | 12/1997 | Rubsamen et al. | 128/200.14 |
| 5,694,920 A | 12/1997 | Abrams et al. | 128/200.16 |
| 5,699,789 A | 12/1997 | Hendricks | 128/203.15 |
| 5,709,202 A | 1/1998 | Lloyd et al. | 128/200.14 |
| 5,718,222 A | 2/1998 | Lloyd et al. | 128/200.14 |
| 5,724,957 A | 3/1998 | Rubsamen et al. | 128/200.14 |
| 5,724,959 A | 3/1998 | McAughey et al. | 128/203.15 |
| 5,727,546 A | 3/1998 | Clarke et al. | 128/203.15 |
| 5,735,263 A | 4/1998 | Rubsamen et al. | 128/200.14 |
| 5,740,793 A | 4/1998 | Hodson et al. | 128/203.15 |
| 5,743,250 A | 4/1998 | Gonda et al. | 128/200.14 |
| 5,743,252 A | 4/1998 | Rubsamen et al. | 128/200.14 |
| 5,755,218 A | 5/1998 | Johansson et al. | 128/200.14 |
| 5,767,068 A | 6/1998 | VanDevanter et al. | 514/9 |
| 5,770,152 A | 6/1998 | Schuster et al. | 422/73 |
| 5,785,049 A | 7/1998 | Smith et al. | 128/203.15 |
| 5,792,057 A | 8/1998 | Rubsamen et al. | 600/431 |
| 5,813,397 A | 9/1998 | Goodman et al. | 128/200.14 |
| 5,819,726 A | 10/1998 | Rubsamen et al. | 128/200.14 |
| 5,823,178 A | 10/1998 | Lloyd et al. | 128/200.14 |
| 5,823,434 A | 10/1998 | Cooper | 239/102.2 |
| 5,826,570 A | 10/1998 | Goodman et al. | 128/200.14 |
| 5,829,435 A | 11/1998 | Rubsamen et al. | 128/203.21 |
| 5,829,436 A | 11/1998 | Rubsamen et al. | 128/200.14 |
| 5,855,564 A | 1/1999 | Ruskewicz et al. | 604/62 |
| 5,857,456 A | 1/1999 | Sun et al. | 128/203.15 |
| 5,871,010 A | 2/1999 | Datta et al. | 128/203.15 |
| 5,873,358 A | 2/1999 | Gonda et al. | 128/200.14 |
| 5,875,776 A | 3/1999 | Vaghefi | 128/203.15 |
| 5,884,620 A | 3/1999 | Gonda et al. | 128/200.14 |
| 5,888,477 A | 3/1999 | Gonda et al. | 424/45 |
| 5,894,841 A | 4/1999 | Voges | 128/203.12 |
| 5,906,202 A | 5/1999 | Schuster et al. | 128/203.23 |
| D410,541 S | 6/1999 | Moulin | D24/110 |
| 5,910,301 A | 6/1999 | Farr et al. | 424/45 |
| 5,915,378 A | 6/1999 | Lloyd et al. | 128/200.22 |
| 5,921,237 A | 7/1999 | Eisele et al. | 128/203.21 |
| 5,934,272 A | 8/1999 | Lloyd et al. | 128/200.22 |
| 5,938,118 A | 8/1999 | Cooper | 239/102.2 |
| 5,941,240 A | 8/1999 | Gonda et al. | 128/200.14 |
| 5,957,124 A | 9/1999 | Lloyd et al. | 128/200.22 |
| 5,960,609 A | 10/1999 | Abrams et al. | 53/428 |
| 5,960,792 A | 10/1999 | Lloyd et al. | 128/203.22 |
| 5,970,973 A | 10/1999 | Gonda et al. | 128/200.14 |
| 5,971,951 A | 10/1999 | Ruskewicz et al. | 604/62 |
| 5,975,076 A | 11/1999 | Yianneskis et al. | 128/203.15 |
| 5,993,783 A | 11/1999 | Eljamal et al. | 424/46 |
| 6,012,450 A | 1/2000 | Rubsamen | 128/200.14 |
| 6,012,454 A | 1/2000 | Hodson et al. | 128/203.15 |
| 6,014,969 A | 1/2000 | Lloyd et al. | 128/200.14 |
| 6,024,090 A | 2/2000 | Gonda et al. | 128/204.23 |
| 6,026,809 A | 2/2000 | Abrams et al. | 125/203.15 |
| 6,029,663 A * | 2/2000 | Eisele et al. | 128/203.21 |
| 6,051,551 A | 4/2000 | Hughes et al. | 514/3 |
| 6,062,214 A | 5/2000 | Howlett | 128/200.23 |
| 6,063,138 A | 5/2000 | Hanna et al. | 23/295 R |
| 6,065,509 A | 5/2000 | Bonney et al. | 141/71 |
| 6,070,575 A | 6/2000 | Gonda et al. | 128/203.12 |
| 6,080,762 A | 6/2000 | Allen et al. | 514/337 |
| 6,085,753 A | 7/2000 | Gonda et al. | 128/898 |
| 6,089,227 A | 7/2000 | Nilsson | 128/203.15 |
| 6,095,134 A | 8/2000 | Sievers et al. | 128/200.14 |
| 6,095,141 A | 8/2000 | Armer et al. | 128/204.26 |
| 6,095,142 A | 8/2000 | Giorgini | 128/205.23 |
| 6,098,615 A | 8/2000 | Lloyd et al. | 128/200.14 |
| 6,098,620 A | 8/2000 | Lloyd et al. | 128/204.23 |
| 6,102,035 A | 8/2000 | Asking et al. | 128/203.15 |
| 6,109,261 A | 8/2000 | Clarke et al. | 128/203.15 |
| 6,116,238 A | 9/2000 | Jackson et al. | 128/203.15 |
| 6,119,953 A | 9/2000 | Gañán-Calvo et al. | 239/8 |
| 6,123,068 A | 9/2000 | Lloyd et al. | 128/200.24 |
| 6,131,567 A | 10/2000 | Gonda et al. | 128/200.14 |
| 6,131,570 A | 10/2000 | Schuster et al. | 128/203.26 |
| 6,142,146 A | 11/2000 | Abrams et al. | 128/203.15 |
| 6,143,277 A | 11/2000 | Ashurst et al. | 424/45 |
| 6,152,130 A | 11/2000 | Abrams et al. | 128/204.21 |
| 6,167,880 B1 | 1/2001 | Gonda et al. | 128/200.14 |
| 6,182,655 B1 | 2/2001 | Keller et al. | 128/203.15 |
| 6,192,876 B1 | 2/2001 | Denyer et al. | 125/205.25 |
| 6,192,882 B1 | 2/2001 | Gonda | 128/203.21 |
| 6,196,218 B1 | 3/2001 | Voges | 128/200.14 |
| 6,208,065 B1 | 3/2001 | Ueyama | 310/328 |
| 6,209,538 B1 | 4/2001 | Casper et al. | 128/203.15 |
| 6,230,706 B1 | 5/2001 | Gonda et al. | 128/203.12 |
| 6,237,590 B1 | 5/2001 | Leedom et al. | 128/203.15 |
| 6,250,298 B1 | 6/2001 | Gonda et al. | 128/200.14 |
| 6,263,872 B1 | 7/2001 | Schuster et al. | 128/203.26 |
| 6,271,206 B1 | 8/2001 | Pillai et al. | 514/44 |
| 6,288,360 B1 | 9/2001 | Beste | 219/121.71 |
| 6,295,986 B1 | 10/2001 | Patel et al. | 128/203.12 |
| 6,328,033 B1 | 12/2001 | Avrahami et al. | 128/203.15 |
| 6,335,316 B1 | 1/2002 | Hughes et al. | 514/12 |
| 6,348,209 B2 | 2/2002 | Placke et al. | 624/435 |
| 6,349,719 B2 | 2/2002 | Gonda | 128/200.14 |
| 6,351,984 B1 | 3/2002 | Srinivasan | 73/40.7 |
| 6,351,987 B1 | 3/2002 | Winston et al. | 73/53.01 |
| 6,354,516 B1 | 3/2002 | Patel et al. | 239/331 |
| 6,369,354 B1 | 4/2002 | Beste | 219/121 |
| 6,428,809 B1 | 8/2002 | Abrams et al. | 424/451 |
| 6,651,341 B1 | 11/2003 | Myrman et al. | 30/2 |

| | | | |
|---|---|---|---|
| 6,702,683 B2 | 3/2004 | Abrams et al. ............. 424/456 |
| 6,845,772 B2 | 1/2005 | Braithwaite et al. ... 128/203.15 |
| 6,889,690 B2 | 5/2005 | Hickey et al. |
| 6,929,004 B1* | 8/2005 | Bonney et al. ........ 128/203.15 |
| 6,971,383 B2 | 12/2005 | Hickey et al. |
| 6,974,032 B2* | 12/2005 | Intini ......................... 206/532 |
| 7,080,644 B2* | 7/2006 | Gumaste ................ 128/203.21 |
| 2001/0007853 A1 | 7/2001 | Dimarchi et al. .............. 514/3 |
| 2001/0053761 A1 | 12/2001 | Dimarchi et al. .............. 514/3 |
| 2002/0162768 A1* | 11/2002 | Bolnick et al. ............. 206/532 |
| 2003/0041859 A1 | 3/2003 | Abrams et al. |
| 2004/0025877 A1 | 2/2004 | Crowder et al. |
| 2004/0050860 A1 | 3/2004 | Crowder et al. |
| 2004/0055598 A1 | 3/2004 | Crowder et al. |
| 2004/0093835 A1* | 5/2004 | Siegel et al. .................. 53/452 |
| 2004/0123864 A1 | 7/2004 | Hickey et al. |
| 2004/0153262 A1 | 8/2004 | Hickey et al. |
| 2005/0103337 A1 | 5/2005 | Hickey et al. |
| 2005/0126569 A1* | 6/2005 | Crowder et al. ....... 128/203.15 |
| 2005/0178382 A1 | 8/2005 | Anderson et al. |

FOREIGN PATENT DOCUMENTS

| | | |
|---|---|---|
| EP | 1106196 A | 6/2001 |
| EP | 1166812 A | 1/2002 |
| EP | 1172122 A1 | 1/2002 |
| FR | 1469648 A | 2/1967 |
| GB | 2264237 A | 8/1993 |
| WO | WO99/65551 | 12/1999 |
| WO | WO 01/68169 * | 9/2001 |
| WO | WO 01/68169 A | 9/2001 |
| WO | WO 01/68169 A1 | 9/2001 |
| WO | WO03/080339 A | 10/2003 |
| WO | WO2004/045957 A | 6/2004 |
| WO | PCT/US2004/035424 | 10/2004 |
| WO | PCT/US2004/035433 | 10/2004 |
| WO | WO 2005002654 A2 | 1/2005 |
| WO | WO 2005002654 A3 | 1/2005 |
| WO | WO2005/044173 | 5/2005 |

OTHER PUBLICATIONS

Brown et al., *Piezo-Electronic Inhaler*, Drug Delivery Technology, vol. 4, No. 8, pp. 90-93, (Oct. 2004).

Crowder et al., *2001: an Odyssey in Inhaler Formulation and Design*, Pharmaceutical Technology, pp. 99-113 (Jul. 2001).

Hickey et al., *A new millennium for inhaler technology*, 21 Pharm. Tech., n. 6, pp. 116-125 (1997).

Peart et al., *New Developments in Dry Powder Inhaler Technology*, American Pharmaceutical Review, vol. 4, n.3, pp. 37-45 (2001).

Prime et al., *Review of Dry Powder Inhalers*, 26 Adv. Drug Delivery Rev., pp. 51-58 (1997).

Wolff et al., *Generation of Aerosolized Drugs*, J. Aerosol. Med. pp. 89-106 (1994).

http://advair.ibreathe.com/consumer/2_2_2_taking_advair_animation.htm, Advair Diskus 100/50, 3 sheets (1997).

http://aventis.co.uk/main/0,1003,EN-GB-29939-48165—,FF.html, Aventis Pharma UK, Dry Powder Inhaler (DPI) Delivery Platforms, 1 sheet, 2005.

Crowder et al., *2001: an Odyssey in Inhaler Formulation and Design*, Pharmaceutical Technology, pp. 99-113, Jul. 2001.

PCT International Search Report and the Written Opinion, PCT/US2004/035433, mailed Mar. 9, 2005.

\* cited by examiner

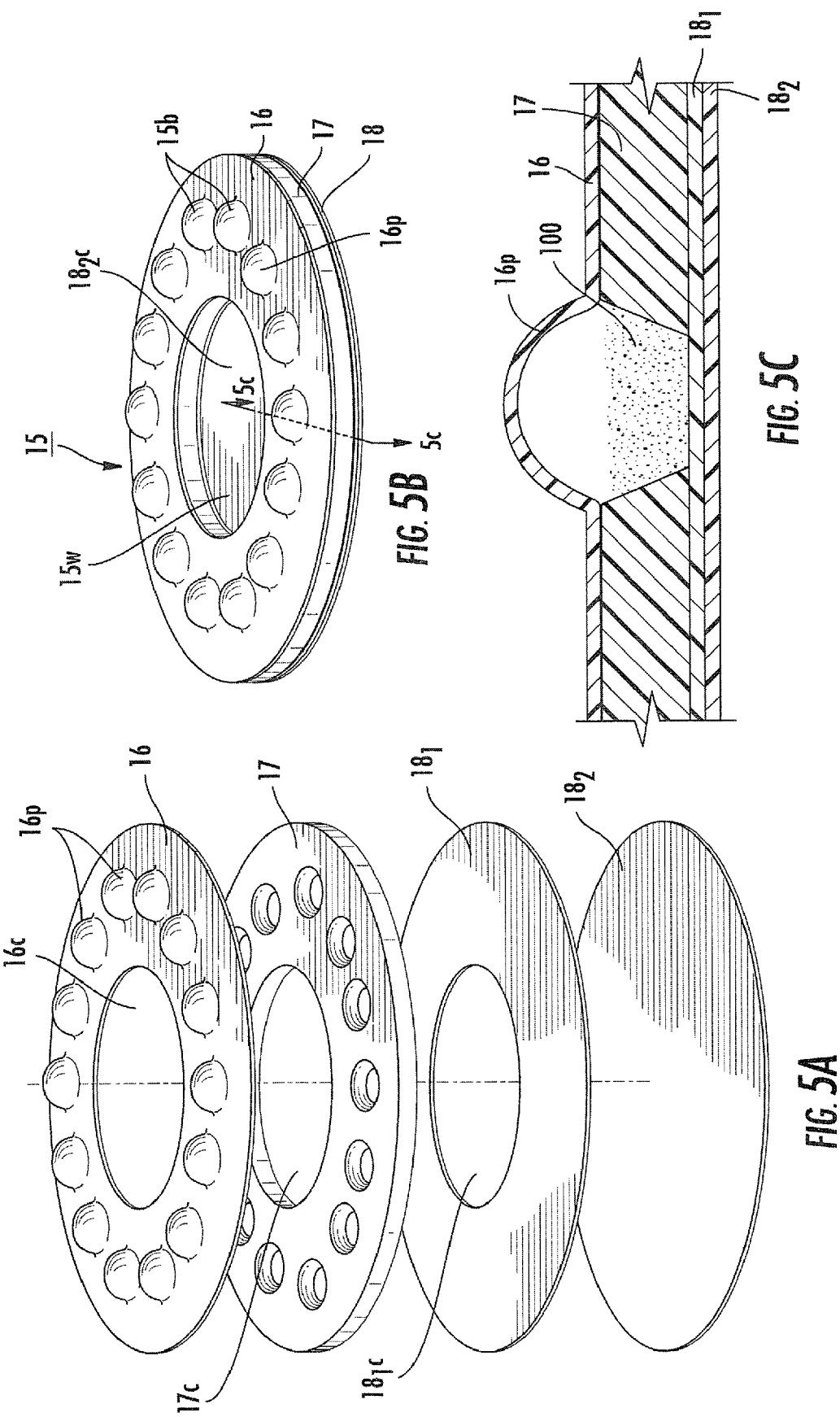

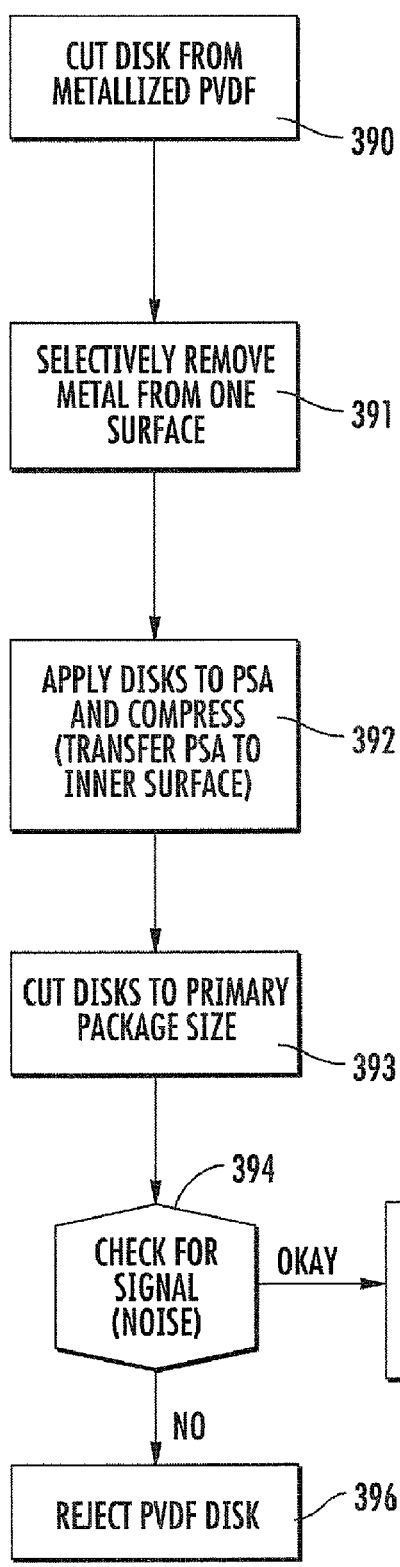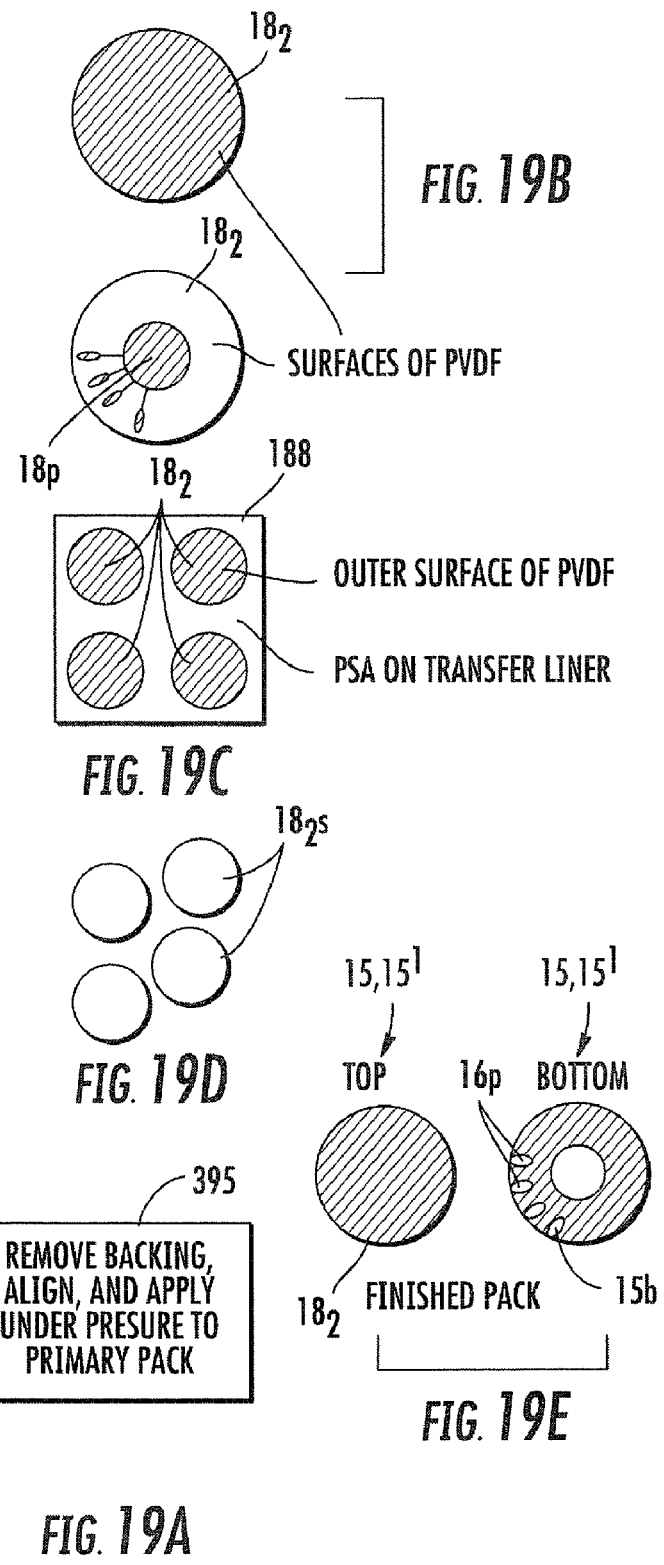

BLISTER PACKAGES WITH FRAMES AND ASSOCIATED METHODS OF FABRICATING DRY POWDER DRUG CONTAINMENT SYSTEMS

RELATED APPLICATION

This application claims priority to U.S. Provisional Application Ser. No. 60/514,727, filed Oct. 27, 2003, the contents of which are hereby incorporated by reference as if recited in full herein.

FIELD OF THE INVENTION

The present invention relates to drug containment systems suitable for dry powders formulated for delivery as inhalant aerosols.

BACKGROUND OF THE INVENTION

Dry powder inhalers (DPI's) represent a promising alternative to pressurized pMDI (pressurized meted dose inhaler) devices for delivering drug aerosols without using CFC propellants. See generally, Crowder et al., 2001*: an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients. Conventionally, many DPIs have operated passively, relying on the inspiratory effort of the patient to dispense the drug provided by the powder. Unfortunately, this passive operation can lead to poor dosing uniformity because inspiratory capabilities can vary from patient to patient (and sometimes even use-to-use by the same patient, particularly if the patient is undergoing an asthmatic attack or respiratory-type ailment which tends to close the airway).

Generally described, known single and multiple dose dry powder DPI devices use: (a) individual pre-measured doses, such as capsules containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form (such as a particulate size) of the dry powder into a patient's airway and direct it to a desired deposit site(s). If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, many dry powder inhalers can retain a significant amount of the drug within the device, which can be especially problematic over time. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of these patents are hereby incorporated by reference as if stated in full herein.

More recently, Hickey et al., in U.S. patent application Ser. No. 10/434,009 and PCT Patent Publication No. WO 01/68169A1 and related U.S. National Stage patent application Ser. No. 10/204,609, have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems. The contents of these documents are hereby incorporated by reference as if recited in full herein.

Notwithstanding the above, there remains a need for alternative blister packages that can be used with dry powder inhalers.

SUMMARY OF EMBODIMENTS OF THE INVENTION

Embodiments of the present invention provide blister packages that can be used with dry powder inhalers. The blister packages may be configured to employ active piezoelectric polymer-driven dispersion. Other embodiments are related to methods of fabricating blister packages that can be used in inhalers.

Certain embodiments are directed to multi-dose blister packages having a plurality of blisters thereon and adapted for use in an inhaler. The blister packages include: (a) a substantially rigid intermediate member having opposing top and bottom surfaces with a plurality of spaced apart gap spaces formed therethrough, a respective one gap space configured to define at least portion of a sidewall of a respective blister; (b) a ceiling attached to the top surface of the intermediate member so that the ceiling extends above each gap space to define a top of each blister; and (c) a floor comprising a flexible material attached to the bottom surface of the intermediate layer so that the floor extends under each gap space to define a bottom of each blister.

In particular embodiments, the ceiling comprises a flexible material having sufficient structural rigidity so that the ceiling is able to define a plurality of spaced apart projections therein. In some embodiments, the floor comprises a piezoelectric polymer and the blister package further includes a bolus quantity of dry powder disposed in respective blisters.

Other embodiments are directed to multi-dose blister packages adapted for use in an inhaler. The blister packages include: (a) a frame member having a plurality of spaced apart apertures; (b) a ceiling having a corresponding plurality of spaced apart projections, the ceiling disposed under the frame and aligned so that a respective ceiling projection extends through and rises above a respective frame aperture; and (c) a flexible floor underlying and attached to the ceiling, wherein the ceiling and floor are configured to define a plurality of spaced apart sealed blisters therebetween.

In particular embodiments, the frame member is configured to resist flexure, and the floor comprises a piezoelectric polymer material. The frame member can have a substantially planar body with sufficient rigidity to remain substantially planar during operation. In certain embodiments, the ceiling is a substantially continuous layer that is sized and configured to extend over all of the blisters under the frame member with the projections aligned to reside in the frame member apertures.

Other embodiments are directed to methods for fabricating a multi-dose blister package having a plurality of blisters thereon that is adapted for use in an inhaler. The method includes: (a) providing a substantially rigid intermediate member having opposing top and bottom surfaces with a plurality of spaced apart gap spaces formed therethrough, a respective gap space configured to define at least a portion of a sidewall of a respective blister; (b) attaching a ceiling to the top surface of the intermediate member so that, in operation, the ceiling extends above each gap space to define a top of each blister; (c) disposing or positioning a quantity of dry powder in the blisters; and (d) sealing a floor comprising a flexible material to the bottom surface of the intermediate member so that the floor extends under each gap space to define a bottom of each blister.

Still other methods making a multi-dose blister package adapted for use in an inhaler include: (a) providing a frame member having a plurality of spaced apart apertures; (b) forming a plurality of spaced apart wells in a ceiling that, in position on a sealed blister package, define projections; (c) positioning a ceiling having the spaced apart wells above the frame and aligned therewith so that a respective ceiling well extends through and falls below a respective frame aperture; (d) placing a quantity of dry powder in the ceiling wells; and (e) sealing a flexible floor to the ceiling to define a plurality of spaced apart sealed blisters therebetween.

In particular embodiments, the frame member can be configured to resist flexure and the floor can comprise a piezoelectric polymer material.

It is noted that aspects of the invention may be embodied as hardware, software or combinations of same, i.e., devices and/or computer program products. These and other objects and/or aspects of the present invention are explained in detail in the specification set forth below.

BRIEF DESCRIPTION OF THE DRAWINGS

FIG. 5A is an exploded view of another blister package according to embodiments of the present invention.

FIG. 5B is a perspective view of the blister package shown in FIG. 5A assembled.

FIG. 5C is an enlarged side sectional view of a portion of the blister package shown line 5C-5C in FIG. 5B illustrating a blister according to embodiments of the present invention.

FIG. 19A is a flow chart of operations that can be carried out to fabricate a laminated floor of a blister package according to embodiments of the present invention.

FIGS. 19B-19E illustrate a serial progression of configurations of piezoelectric floors suitable for a blister package during the fabrication operations shown in FIG. 19A.

DESCRIPTION OF EMBODIMENTS OF THE INVENTION

Figure 1A:
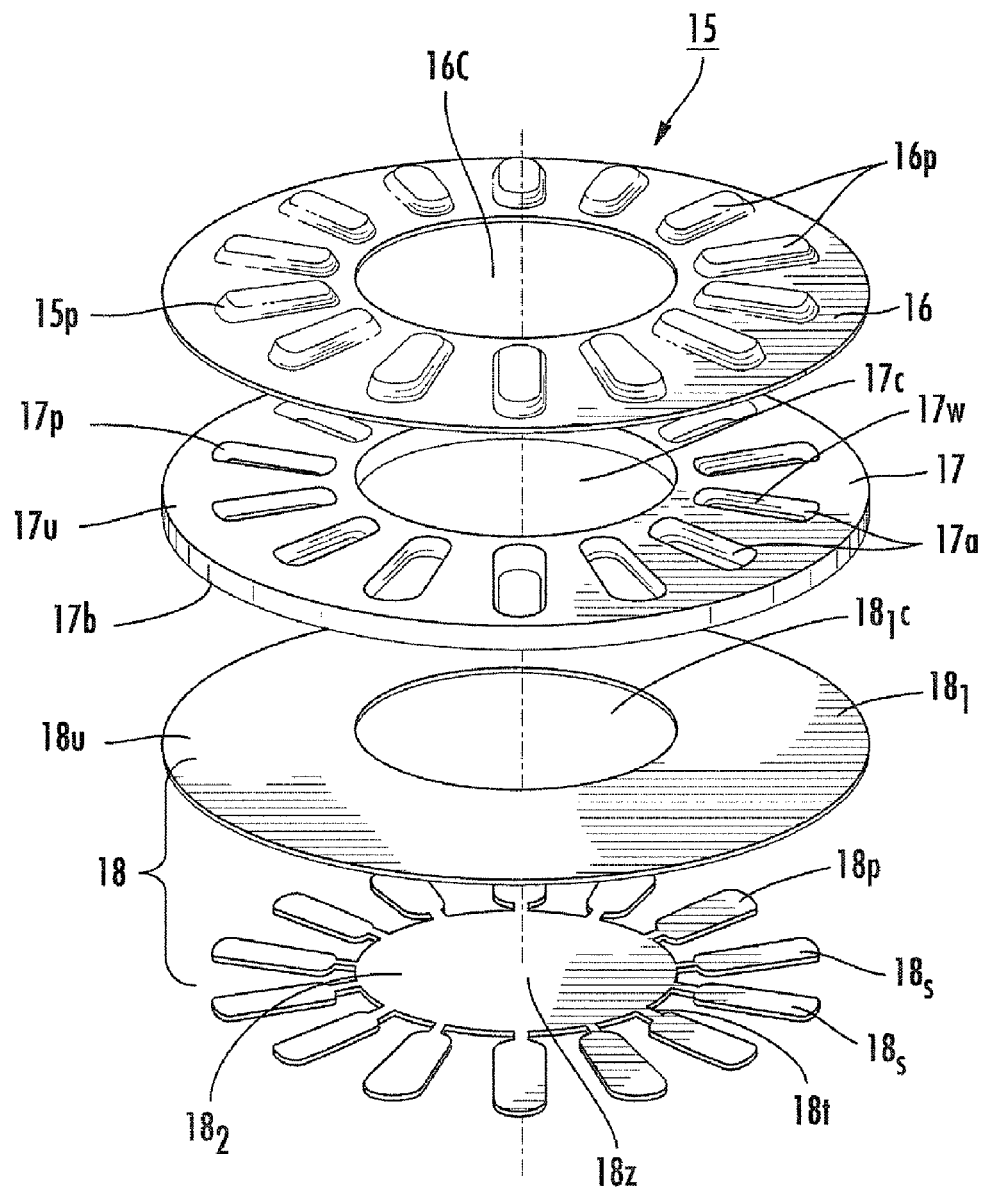
FIG. 1A is an exploded view of an exemplary blister package according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Where used, the terms "attached", "connected", "contacting", and the like, can mean either directly or indirectly, unless stated otherwise.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

It will be understood that the spatially relative terms are intended to encompass different orientations of the device in use or operation in addition to the orientation depicted in the figures. For example, if a blister package shown in the figures oriented upward is inverted (turned over), elements described as "below" or "beneath" other elements or features would then be oriented "above" the other elements or features. Thus, the exemplary term "below" can encompass both an orientation of above and below. The device may be otherwise oriented (rotated 90 degrees, 180 degrees, or at other orientations) and the spatially relative descriptors (such as, but not limited to, vertical, horizontal, above, upper, lower, below and the like) used herein interpreted accordingly.

The term "blister" means a sealed dry powder well or receptacle that can hold a (typically meted bolus) quantity of a dry powder, typically a dry powder medicament. The term "blister package" describes a device (such as a card) that holds a plurality of sealed blisters and may be also known as a drug containment system ("DCS"). The blisters may be configured with a projecting ceiling as will be described further below, or configured in other suitable geometries.

The devices and methods of the present invention may be particularly suitable for holding doses of dry powder substances that are formulated for in vivo inhalant dispersion (using an inhaler) to subjects, including, but not limited to, animal and, typically, human subjects. The dry powder substance may include one or more active pharmaceutical constituents as well as biocompatible additives that form the desired formulation or blend. As used herein, the term "dry powder" is used interchangeably with "dry powder formulation" and means the dry powder can comprise one or a plurality of constituents or ingredients with one or a plurality of (average) particulate size ranges. The term "low-density" dry powder means dry powders having a density of about 0.8 $g/cm^3$ or less. In particular embodiments, the low-density powder may have a density of about 0.5 $g/cm^3$ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aerorolization delivery to the desired systemic target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated with embodiments of the invention include, but are not limited to, asthma, COPD (chronic obstructive pulmonary disease), viral or bacterial infections, influenza, allergies, and other respiratory ailments as well as diabetes and other insulin resistance disorders. The dry powder inhalation may be used to deliver locally acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhaler will vary depending on the patient size, the systemic target, and the particular drug. Conventional exemplary dry powder dose amount for an average adult is about 10-30 mg and for an average adolescent pediatric subject is from about 5-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends. Further, the dry powder formulations may be configured as a smaller administerable dose compared to the conventional 10-25 mg doses. For example, each administerable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular dose receptacle may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In certain embodiments, certain active elements are integral to/included as part of a disposable (replaceable) blister package. In other embodiments, the inhaler with the drug blister package can itself be disposable after dispensing the doses provided by a blister package. Unlike many conventional active dispersion systems, cleansing of the active mechanism portion of the inhaler may not be required. Examples of suitable inhalers are described in co-pending U.S. patent application Ser. No. 10/434,009 and Provisional U.S. Patent Application Ser. No. 60/514,671, the contents of these documents are hereby incorporated by reference as if recited in full herein.

Figure 2:
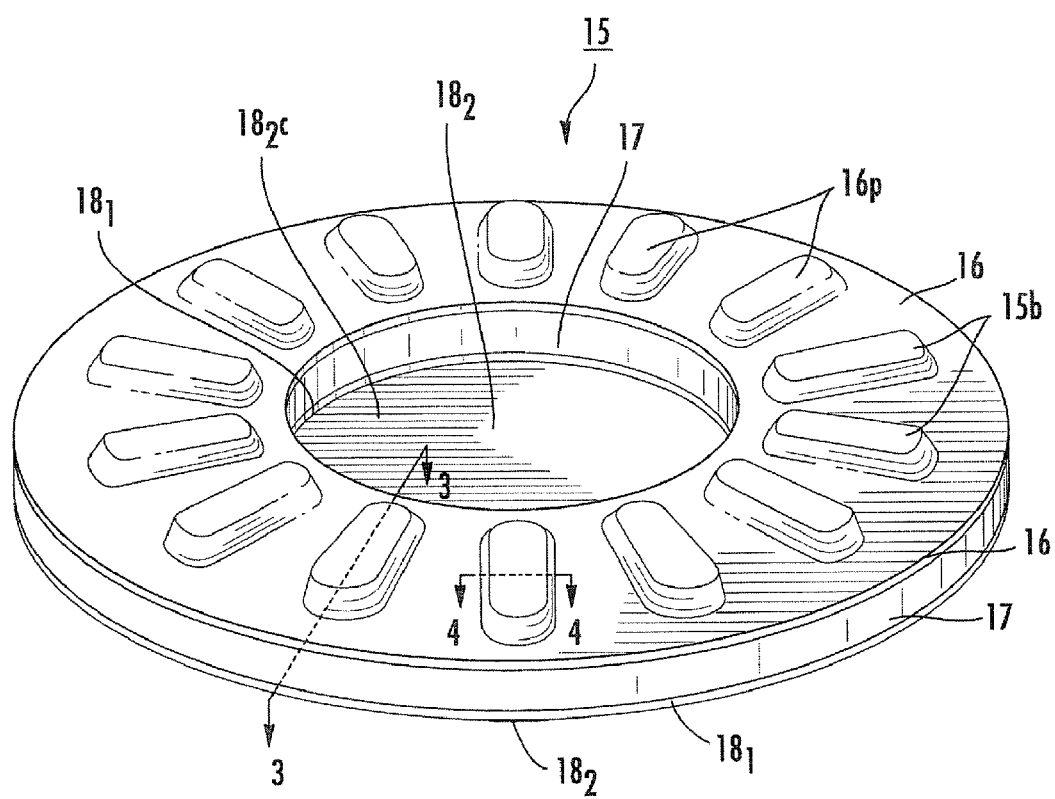
FIG. 2 is an enlarged perspective view of an assembled blister package according to embodiments of the present invention.

FIGS. 1A and 2 illustrate one exemplary blister package 15. As shown in FIG. 2, the blister package 15 includes a plurality of spaced apart blisters 15b. The blister package 15 can include a ceiling 16 with projections 16p (i.e., wells) overlying each blister 15b, an intermediate (a.k.a., "spacer") member 17 and a floor 18. The intermediate member 17 can have a thickness that is greater than the combined thickness of the ceiling and floor 16, 18, respectively. Typically, the intermediate member 17 will have a thickness that is at least five times, and typically at least about ten times, and more typically at least about 15 times, greater than the thickness of either the floor 18 or ceiling 16. Although shown with projections 16p formed therein, in particular embodiments, the ceiling 16 may also be substantially planar over the apertures of the spacer member 17 (and/or over the entire surface of the spacer member 17).

Figure 4A:
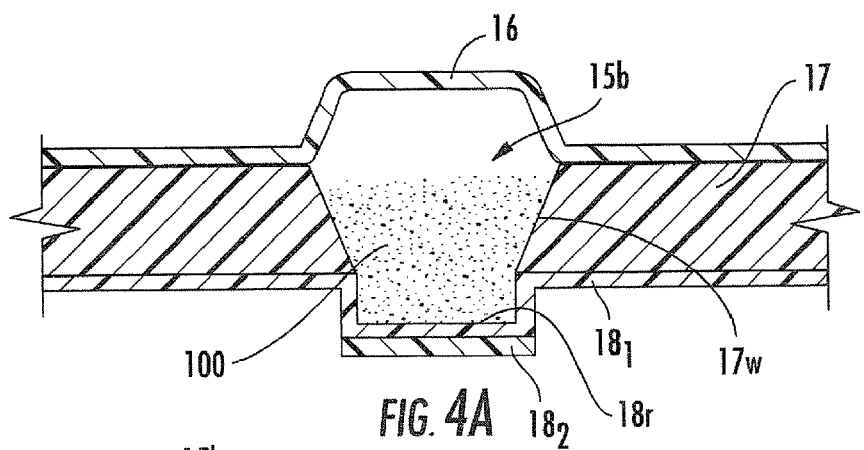
FIG. 4A is an enlarged side sectional view of a portion of a blister package taken along line 4-4 of FIG. 2, illustrating a blister according to embodiments of the present invention.
Figure 4B:
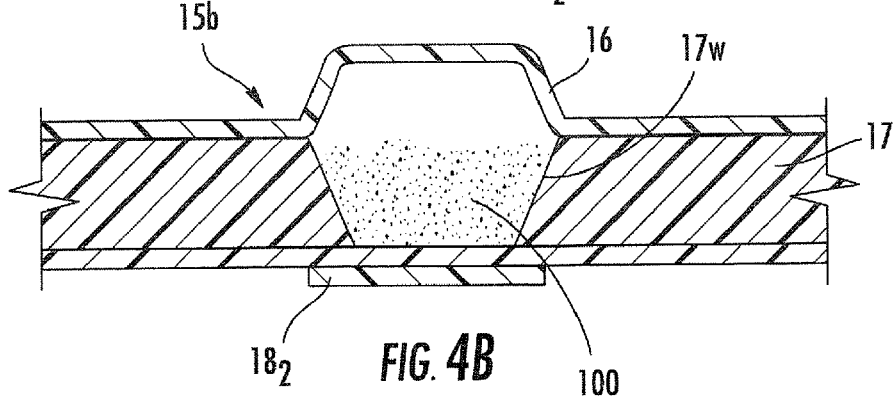
FIG. 4B is an enlarged side sectional view of a portion of a blister package taken along line 4-4 of FIG. 2, illustrating a blister according to other embodiments of the present invention.

In certain embodiments, the ceiling 16 is configured to be removed, when in position in an inhaler, to dispense the dry powder 100 held therein (FIGS. 4A and 4B). The ceiling 16 can comprise a relatively thin flexible material. In certain embodiments, the ceiling 16 comprises a flexible material layer that has sufficient structural rigidity so as to be able to have projections 16p formed therein that retain their shape as shown in FIG. 1 when in position. In addition, the ceiling is typically configured to inhibit moisture penetration to keep the dry powder, dry, for the desired shelf and/or useful life of the dry powder (drug). For example, the ceiling 16 can contain foil (such as aluminum or other suitable material) and/or may be a laminated structure, comprising a polymer layer and a foil layer. In particular embodiments, the ceiling 16 can comprise layers of polyamide film, aluminum foil, and polypropylene film (where the top layer may be the polyamide film) adhered to each other with a laminating adhesive. In certain embodiments, the ceiling 16 can have a thickness of between about 0.100-0.150 mm, and typically about 0.127 mm. The projections 16p, where used, may have a height that is between about 1-5 mm and typically at least about 1.5 mm.

Figure 3:
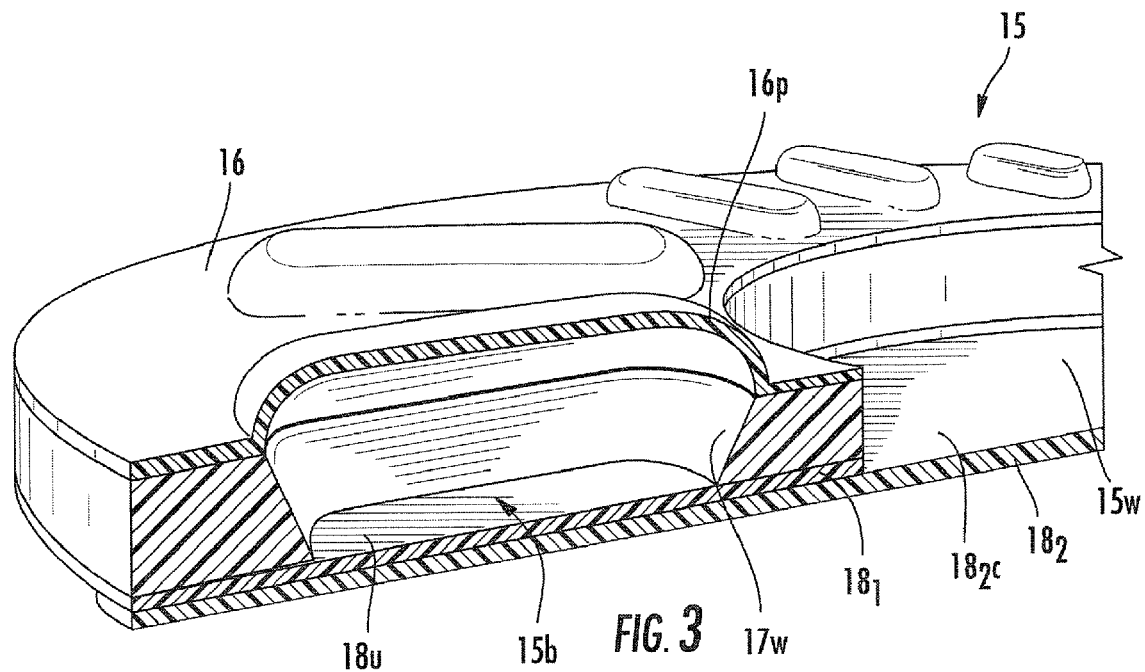
FIG. 3 is a greatly enlarged section view of a portion of the blister package taken along line 3-3 as shown in FIG. 2.

Still referring to FIG. 1A, as shown, the intermediate member 17 includes a plurality of spaced apart gap spaces or apertures 17a extending therethrough, each having a depth that defines at least a portion of a sidewall 17w (FIG. 3) of a blister 15b. Typically, the intermediate member 17 defines substantially the entire (typically all of the) sidewall 17w of a respective blister 15b (see, e.g., FIGS. 4A and 4B) and extends a distance above the floor 18 and below the ceiling 16. The gap space or aperture 17a can include a single sidewall 17w when the geometric shape of the aperture is circular, oval, curvilinear (such as elongate channel) or other continuous shape. Alternatively, in other geometric configurations, the aperture 17a can be configured with a plurality of contiguous sidewalls 17w (i.e., a square, rectangle, triangle, wedge, or other multi-sided shape). FIG. 1A illustrates the aperture 17a having an elongate curvilinear configuration (when viewed from the top and/or bottom). FIGS. 5A-5C illustrate a blister package 15 with a ceiling 16 having semi-spherical projections 16p and an intermediate member 17 having a substantially circular aperture 17a (when viewed from the top and/or bottom).

As shown in FIGS. 4A, 4B, and 5C, the sidewall 17w of the blister 15b can angle or taper inward from top to bottom, with the surface area of the bottom of the aperture 17a being less than that of the top of the intermediate member aperture 17a. In particular embodiments, the sidewall 17w can have an angle of inclination (that may be substantially constant) that is between about 15-60 degrees, and typically between about 20-40 degrees. The sealed blister 15b is illustrated as enclosing a quantity of dry powder 100 therein.

In the embodiment shown in FIG. 1A, the frame apertures 17a have a perimeter shape 17p. The perimeter shape 17p is sized and configured to substantially correspond with the perimeter shape 15p of the blister 15b that is defined by that of the projecting ceiling 16p. Thus, the aperture 17a may have a shape and size that is substantially the same as the shape and size of a respective projecting overlying ceiling 16*p*.

The intermediate member 17 can have increased rigidity with respect to that of the floor 18 and/or ceiling 16. In particular embodiments, the intermediate member 17 can be a substantially rigid light-weight member that provides structural integrity to the ceiling and floor 16, 18. The ceiling 16 can be attached to an upper primary surface 17*u* of the intermediate member 17 and the floor 18 can be attached to a lower primary surface 17*b* of the intermediate member 17. The intermediate member 17 may have a unitary body as shown or a laminated or stacked structure (not shown). In certain embodiments, the intermediate member 17 can be a molded polymer or fiber reinforced resin material. In particular embodiments, the intermediate member 17 comprises a natural homopolymer polypropylene and can typically be between about 1-3 mm thick, and is more typically about 2 mm thick. Other suitable materials or fabrication methods and thicknesses can also be used. The intermediate member 17 may include additional apertures, slots or depressions and the like to further decrease weight as suitable. The intermediate member 17 may be configured with sufficient thickness, material and/or coatings to provide a moisture barrier (inhibit moisture penetration) to the dry powder held in the blister as discussed above for the ceiling.

Figure 1B:
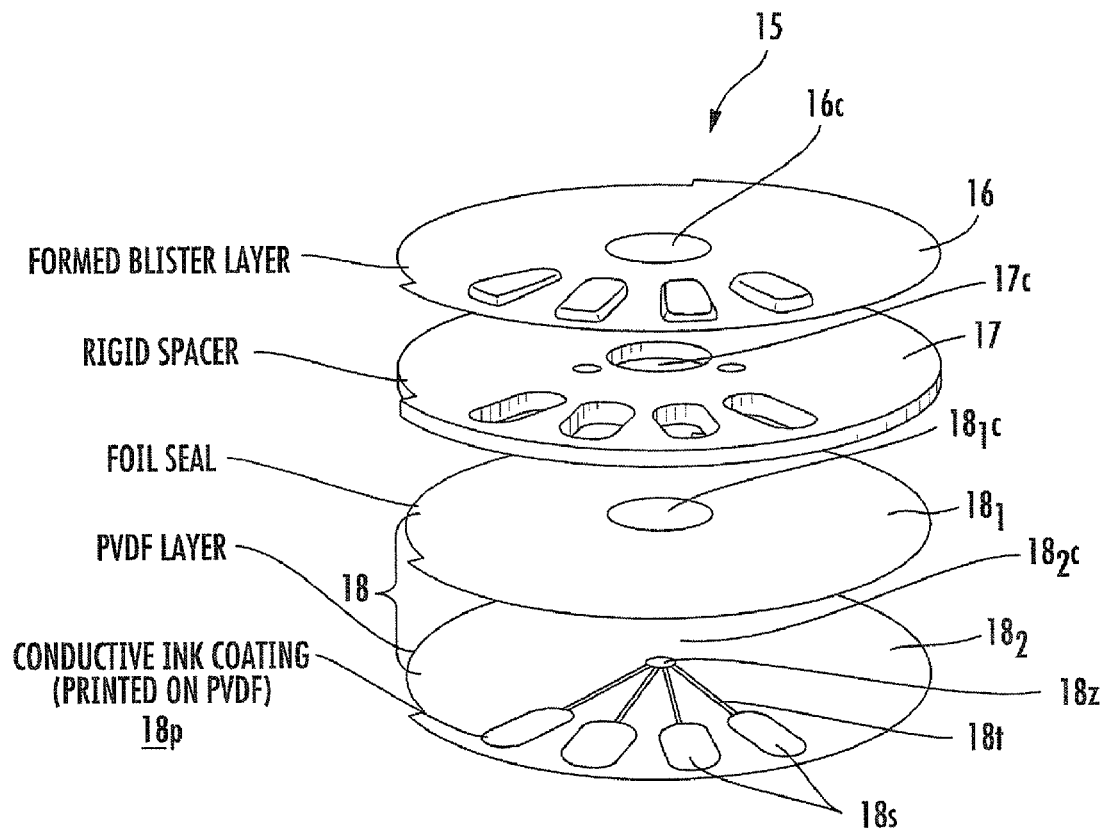
FIG. 1B is an exploded view of another exemplary blister package according to embodiments of the present invention.

The ceiling and floor 16, 18, respectively, can comprise a continuous sheet(s) or layer(s) of material as shown in FIGS. 1A, 1B and 5A. Alternatively, the ceiling and/or floor 16, 18, respectively, may comprise non-continuous discrete segments of material forming a respective blister ceiling 16 and floor 18 that can be attached over and under each intermediate member aperture 17*a* to define respective sealed blisters 15*b* (not shown).

FIGS. 1A and 1B illustrate that the floor 18 can include a plurality of abutting flexible and/or resilient layers 18$_i$, shown as two different layers, a non-active layer 18$_1$ and an active layer 18$_2$. In particular embodiments, the active layer 18$_2$ may be positioned above the non-active layer 18$_1$. The term "active" layer means that the layer comprises an electrically active material. In certain embodiments, the active layer 18$_2$ comprises a thin-film layer of a piezoelectric material, typically a polymer such as PVDF as will be described further below. In certain embodiments, additional floor layers may also be used (not shown). Alternatively, the floor 18 can be a single layer configuration defined by the active layer 18$_2$ (also not shown). Similar to the ceiling 16, the floor 18 can be configured to inhibit moisture penetration (i.e., be configured to provide a moisture barrier at operating/exposure pressures for a desired length of time) into the blister space thereby keeping the dry powder dry and ready for flowable dispersion via inhalation. In addition, the portions of the floor 18 (i.e., such as the upper surface) that contacts the dry powder should be configured to be compatible therewith (i.e., chemically and/or physically).

Typically, when a plurality of floor layers $\mathbf{18}_i$ are used, the floor layers $\mathbf{18}_i$ (such as, for example $\mathbf{18}_1$, $\mathbf{18}_2$) are attached to each other so that flexure (up and down) of one layer causes the other(s) to substantially concurrently flex up and down in response thereto. The floor layers $\mathbf{18}_i$ can be configured so that the flexing of the active layer $\mathbf{18}_2$ is not substantially reduced or insulated by the other contacting layer (s) to thereby provide a desired vibratory dispersion input to the dry powder 100 in a blister 15*b* during active inspiration. The floor layers $\mathbf{18}_1$, $\mathbf{18}_2$ can be a laminated structure or otherwise attached over a sufficient surface area to facilitate substantially concurrent flexing at a floor 18 of a respective blister 15*b* to thereby vibrate dry powder held therein during operation. The non-active portion or layers of the floor 18 may include material(s) similar to that described for the ceiling 16 above. The floor layers $\mathbf{18}_1$, $\mathbf{18}_2$ may be adhesively attached, heat and/or pressure bonded, or otherwise attached.

The non-active layer $\mathbf{18}_1$ can include foil, typically aluminum foil, and may, in certain embodiments, include a polymer coating or layer on the top and/or bottom thereof. Typically the non-active portion of the floor $\mathbf{18}_1$ will be at least about 20 microns thick. Coatings and/or other materials can be used to inhibit moisture penetration (i.e., act as a moisture barrier) into the sealed blister cavity and/or to aid in sealing (i.e., adhering) the floor 18 to adjacent structures or layers. One suitable material is available from Hueck Foils, located in Blythewood, S.C.

In particular embodiments, the non-active layer $\mathbf{18}_1$ may be attached using a relatively thin foil-release material such as a release film. The release film can be used to transfer a pressure sensitive adhesive (PSA) to a desired layer (such as shown in FIG. 19C) that can be used to attach two layers together. The upper surface 18*u* of the non-active layer $\mathbf{18}_2$ may define the dry powder contact surface of the blister 15*b* as shown in FIG. 3 and can be attached to the active layer $\mathbf{18}_2$ that can comprise the piezoelectrically active material.

As shown in FIGS. 1A and 1B, the active layer $\mathbf{18}_2$ can be configured with a predetermined conductive pattern 18*p*. The pattern 18*p* can include a plurality of spaced apart segments 18*s* sized, configured and aligned to be positioned under a bottom of each blister 15*b*. The pattern 18*p* can also include at least one electrical (signal) trace 18*t* leading from the segment 18*s* to an electrical contact zone 18*z*. The electrical contact zone 18*z* is shown as centrally positioned on the active layer $\mathbf{18}_2$; however, other electrical contact zone configurations and locations can be used. In those embodiments, alternative access through, on or around the intermediate member 17 may be provided. As such, the intermediate member 17 may be molded or formed into other shapes without a center aperture and/or different access configurations. For example, FIGS. 8D and 8E illustrate conductive patterns 18*p*' with contact zones 18*z* located proximate an outer perimeter of the blister package. FIG. 8D illustrates that each blister may have its own contact zone for individual selective activation (individually addressable blisters) or excitation of a target blister in operation. FIG. 8E illustrates a different blister shape and also that respective pairs of blisters may share a common contact zone 18*z* with traces 18*t* for each blister traveling toward each other and merging to the common contact zone 18*t*. Other numbers of blisters can be electrically grouped and/or the contact zones may be positioned at other locations. The plurality of shared contact zones 18*z*, one for each pair of blisters, may be particularly suitable for use in combinatorial dispersion configurations, such as those shown in FIGS. 7A-7C.

In operation, a predetermined electrical signal can be applied to the active layer $\mathbf{18}_2$ to flex the floor of the blister 15*b* and vibrate the powder 100 held therein (FIGS. 4A, 4B). The electrical signal is transmitted to the blister 15*b* in a dispensing location via the conductive pattern 18*p* (such as via the conductive zone 18*z* to the trace 18*t* and the segment 18*s* under the blister 15*b*). In the embodiment shown in FIGS. 1A and 1B, a plurality of blisters 15*b* may be in electrical communication with a signal generator 200 (FIG. 13) and concurrently flexed. In other embodiments, the predetermined pattern 18*p* can be configured so that a selective blister 15*b* can be flexed (not shown). In the latter, the contact zone 18*z* may be configured as a discrete contact zone for each blister 15*b*. A regional contact zone 18*z* may also be provided to electrically communicate with a plurality of blisters (not shown). Electrical insulation or discontinuous conductive patterns 18*p* can be used to provide electrical separation as is well known to one of skill in the art. The contact zone 18*z* may be otherwise located, such as at an outer or inner edge of the pattern 18*p* to communicate with the signal generator 200. The signal generator 200 (such as that shown in FIG. 13) may be integrated with the blister package 15*b* or held in the inhaler so as to engage the active floor layer 18$_2$ in operation.

The predetermined pattern 18*p* can comprise a conductive material such as metal. The conductive material can be a thin layer of metal or other conductive material that can be inked, stamped, printed (including screen printed), imaged (including, but not limited to, photo-resist imaging), rolled, deposited, sprayed, or otherwise applied to (one or both primary surfaces of) the active layer 18$_2$. Other methods of providing the conductive pattern 18*p* can also be used, including electron beam evaporation, thermal evaporation, painting, dipping, or sputtering a conductive material or metallic paint and the like or material over the selected surfaces of the piezoelectric substrate (preferably a PVDF layer as noted above). In particular embodiments, alternative metallic circuits, foils, surfaces, or techniques can also be employed, such as attaching a conductive mylar layer or flex circuit over the desired portion of the outer surface of the piezoelectric substrate layer. If flex circuits are used, they may be configured or attached to the piezoelectric substrate layer so as to be substantially transparent to the structure to reduce any potential dampening interference with the substrate layer.

Typically, upper and lower surface metal trace patterns are formed on opposing sides of a piezoelectric polymer material layer but do not connect or contact each other. For example, conductive paint or ink (such as silver or gold) can be applied onto the major surfaces of the package about the elongated channels and associated metal traces such that it does not extend over the perimeter edge portions of the piezoelectric substrate layer, thereby keeping the metal trace patterns on the top and bottom surfaces separated with the piezoelectric substrate layer therebetween. This configuration forms the electrical excitation path when connected to a control system to provide the input/excitation signal for creating the electrical field that activates the deformation of the piezoelectric substrate layer during operation. Typically, one pattern 18*p* is applied to one side of the active floor 18$_2$ and the other side may have a different conductive pattern and/or coverage.

Figure 8A:
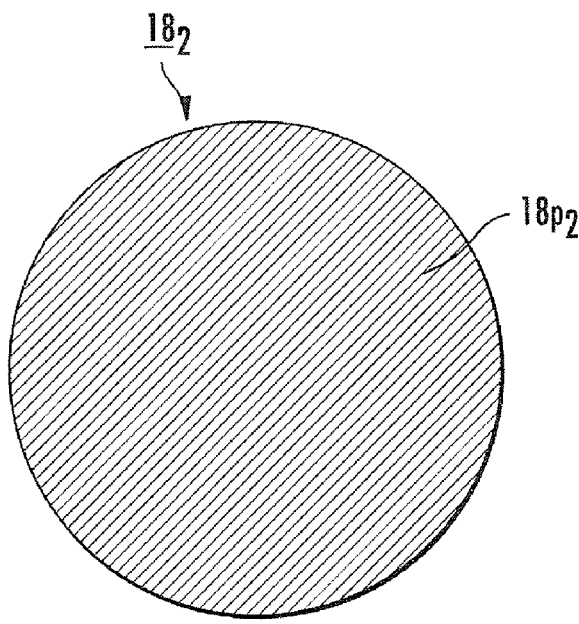
FIG. 8A is a top or bottom view of an exemplary piezoelectric film layer according to embodiments of the present invention.

FIG. 1A illustrates that the active layer 18$_2$ may have a different configuration that the first floor layer 18$_1$. FIGS. 1B and 8A illustrate that the first floor layer 18$_1$, the intermediate member 17 and the ceiling 16 may be configured with substantially the same shape and size (shown as substantially circular) when viewed from the top, and have aligned center spaces or apertures 16*c*, 17*c*, 18$_1$*c*, that when assembled provide an access window 15*w* that exposes a center portion 18$_2$*c* (FIG. 2, 3, 5B) of the top surface of the second or active floor layer 18$_2$. Where edge contact zones or other electrical contact configurations are used, the center window 15*w* to the active layer 18$_2$ may not be used.

FIG. 5C illustrates that the active floor layer 18$_2$ can be substantially coextensive at least about an outer perimeter portion of the blister package 15 while FIGS. 4A and 4B illustrate that the active floor layer 18$_2$ can be discontinuous at the outer perimeter portion of the blister package 15. FIGS. 4B and 5C also illustrate that the floor 18 of a respective blister 15*b* can be substantially planar about the intermediate member gap space or aperture 17*a* while FIG. 4A illustrates that the floor 18 may be configured with a recession 18*r* therein (formed by at least the first layer 18, and in some instances a depression in the piezoactive layer 18$_2$ conformally thereunder (not shown)).

FIG. 1A illustrates that the active layer 18$_2$ may cover or have less surface area than the first floor layer 18$_1$, of the blister package 15. FIG. 1B illustrates that the first and second floor layers 18$_1$, 18$_2$ can be substantially coextensive with each other (at least over a major portion of the configurations thereof away from the center portions) with the first layer 18$_1$, having an aperture 18$_1$c that exposes or provides electrical contact with the underlying active layer 18$_2$. It is noted that FIG. 1B is shown without a full conductive pattern 18*p*. As shown in FIGS. 5A and 8A, the active layer 18$_2$ can be a continuous layer of film that is substantially circular. Other configurations may be used.

Figure 8B:
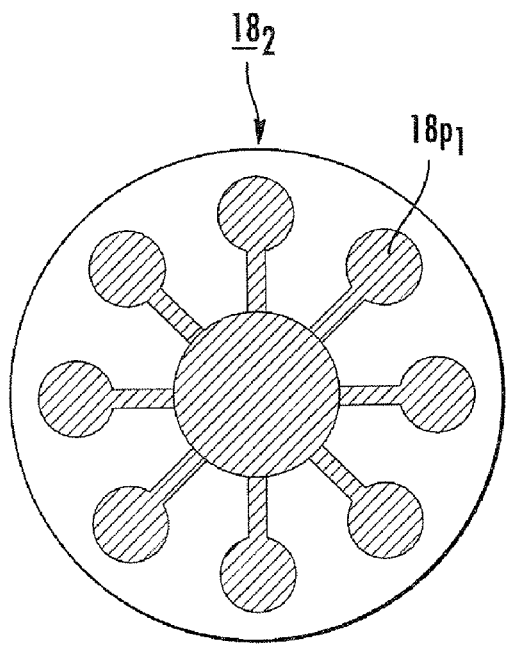
FIGS. 8B and 8C are top or bottom views of examples of a primary surface opposing of the surface shown in FIG. 8A according to embodiments of the present invention.
Figure 8C:
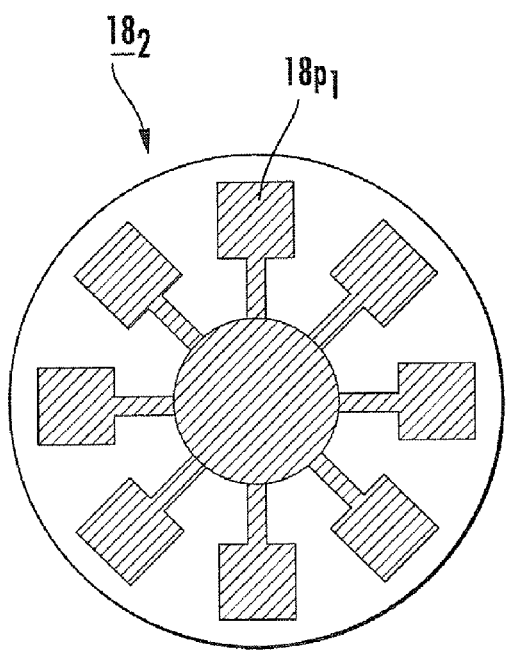
Figure 8D:
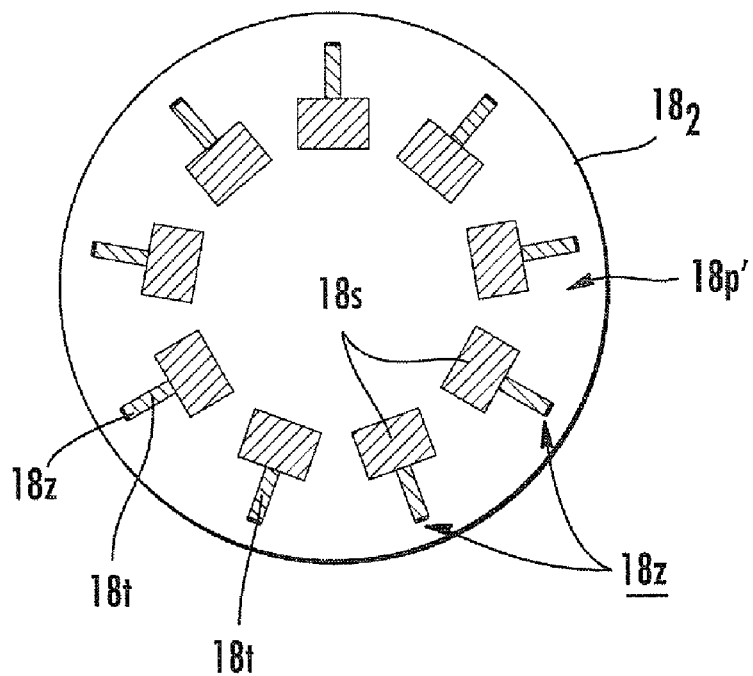
FIG. 8D is a top or bottom view of an alternative conductive pattern layer according to embodiments of the present invention.
Figure 8E:
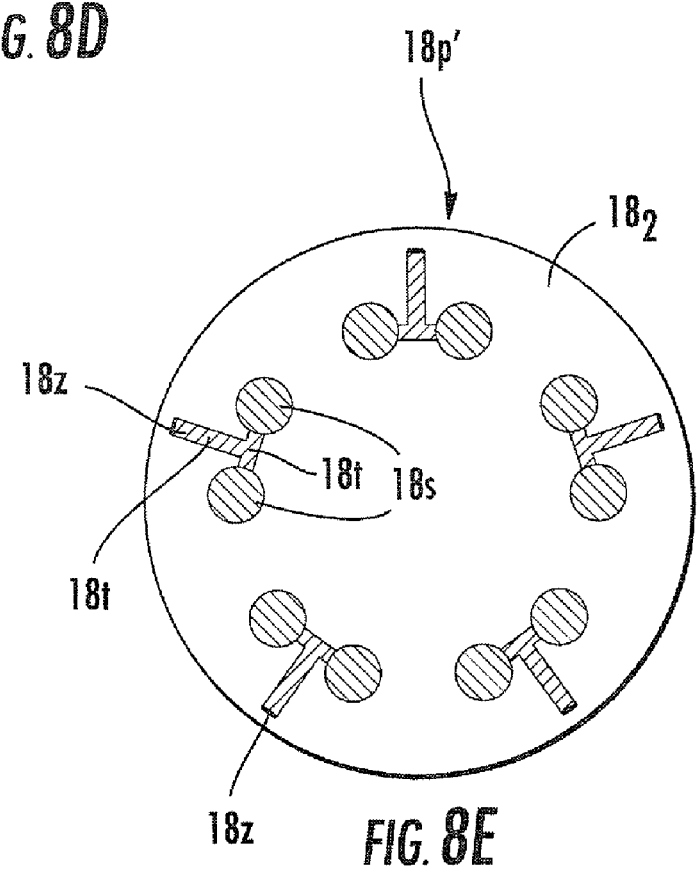
FIG. 8E is a top or bottom view of yet another conductive pattern layer according to embodiments of the present invention.

In the embodiment shown in FIGS. 8A-8C, one of the primary surfaces of the active layer 18$_2$ may have a first predetermined conductive pattern 18*p*$_1$ as shown in FIGS. 8C and 8D while the other surface can have a different second predetermined conductive pattern 18*p*$_2$ as shown in FIG. 8A. The second conductive pattern 18*p*$_2$ shown in FIG. 8A illustrates that substantially the entire primary surface can be conductive (i.e., metallized). In particular embodiments, the first predetermined pattern 18*p*$_1$ may be oriented to be the upper surface configured to contact the underside of the first floor layer 18$_1$, (or the intermediate member 17, where the active layer defines the floor of a blister) with the second pattern 18*p*$_2$ oriented away from the first floor layer 18$_1$. The reverse orientation may be used in other embodiments. Further, as noted above, in yet other embodiments, the second layer 18$_2$ may used without the first layer 18$_1$, so as to define the floor of the blister 15*b*.

In certain embodiments, the active layer 18$_2$ includes a piezoelectric polymer material that can be formed from a piezoelectrically active material such as PVDF (known as KYNAR piezo film or polyvinylidene fluoride) and its copolymers or polyvinylidene difluoride and its copolymers (such as PVDF with its copolymer trifluoroethylene (PVDF-TrFe)).

In particular embodiments, the piezoelectric polymer material comprises a layer of a thin PVDF film. As used herein, the term "thin film" means that the piezoelectric polymer layer is configured as a structurally flexible or pliable layer that can be sized to be about 10-200 μm thick. In certain embodiments, the piezoelectric polymer layer can be sized to be less than about 100 μm thick, typically about 20-60 μm thick, and more typically about 28 μm.

As noted above, selected regions of the piezoelectric polymer material can be coated or layered with a conductive material to form a desired conductive pattern 18*p*. The conductive regions (at least portions of the blister regions) of the floor 18 define the active regions and can be individually or selectively activated during operation. Although shown as forming the bottom layer of the floor 18$_2$, the PVDF may form the bottom, top, or an intermediate layer of the laminated material structure. For intermediate layer configurations, vias and/or edge connections can be used to apply the electric signal to the blister piezoelectric material.

The excitation circuit (signal generating circuitry) configuration can be such that the one surface operates with a positive polarity while the other surface has a negative polarity or ground, or vice versa (thereby providing the electric field/voltage differential to excite the piezoelectric substrate in the region of the selected blister 15*b*). Of course, the polarities can also be rapidly reversed during application of the excitation signal (such as + to −, or + to −) depending on the type of excitation signal used, thereby flexing the piezoelectric material in the region of the receptacle portion. For a more complete discussion of the active excitation path or configuration, see U.S. application Ser. No. 10/204,609, incorporated by reference herein.

Figure 6:
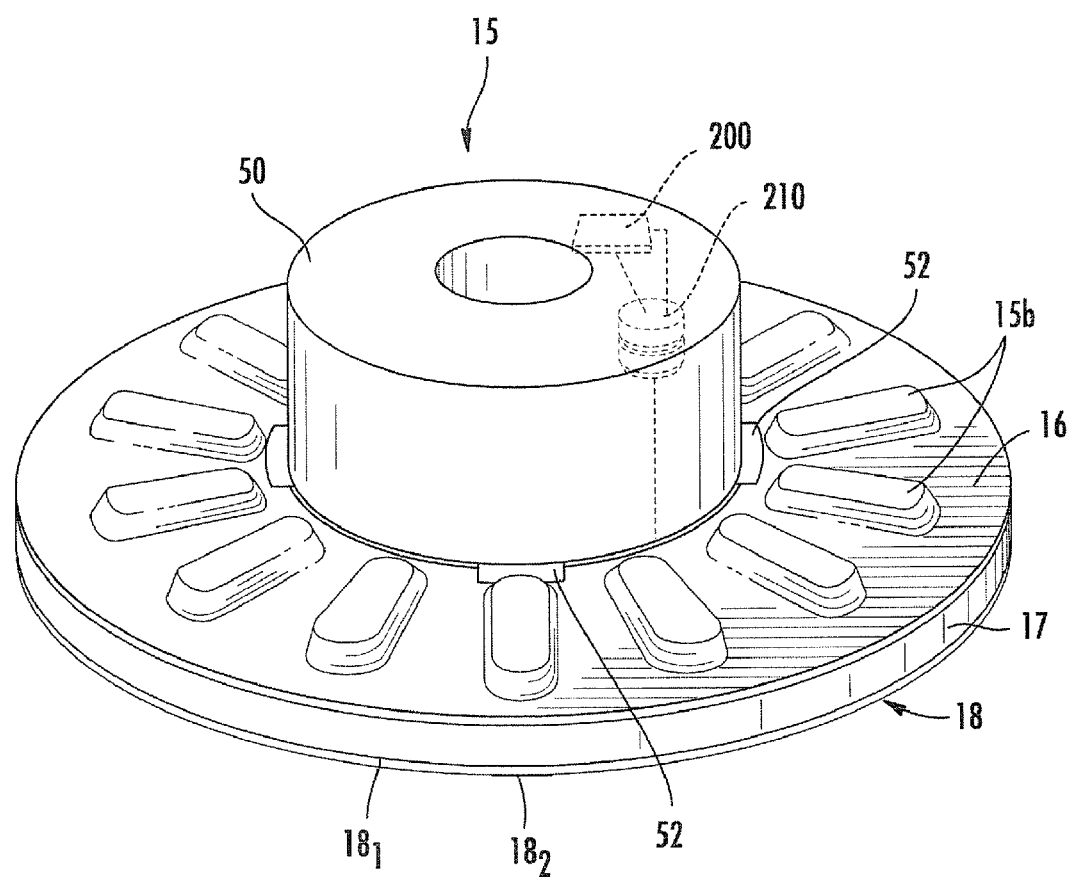
FIG. 6 is a perspective view of a blister package assembly according to embodiments of the present invention.

FIG. 6 illustrates that a mounting member 50 may be attached to the blister package 15. The mounting member 50 can be configured to engage an inhaler to hold the blister package 15 in position therein while allowing the blister package 15 to rotate to present a blister 15b for dispensing via the inhaler. The mounting member 50 may be integrally mounted or formed onto the blister package 15 (by, for example, bonding or molding to the body of the intermediate member 17). The mounting member 50 may be sized and configured to reside over (within and/or above) the blister window 15w. The mounting member 50 may use tabs 52 or other mechanisms to attach to the blister package 15 so that the blister package 15 rotates with the mounting member 50 when in position in the inhaler. FIG. 6 also illustrates that certain operational components can be held by the mounting member 50. For example, a battery 210 (such as a pancake-like and/or small digital camera type battery) and a signal generator 200 or components thereof. The mounting member 50 can include electrical leads or traces that extend from the signal generator 200 to the active floor layer $18_2$. The gear 50g can include a bore 50b therein which can be configured to allow access to an exposed surface of the active layer $18_2$.

In particular embodiments, the mounting member 50 can be configured as a rotatable gear 50g with gear teeth 50t (FIG. 9) that mounts in the inhaler. In operation, a pawl or other indexing mechanism contacts one or more gear teeth 50t to so as to controllably rotate the gear 50g and thereby advance the blister package 15 therewith to position a blister 15b at a blister dispensing location in the inhaler. See co-pending U.S. Provisional Patent Application Ser. No. 60/514,671, the contents of which were hereby incorporated by reference above as if recited in full herein.

Figure 7A:
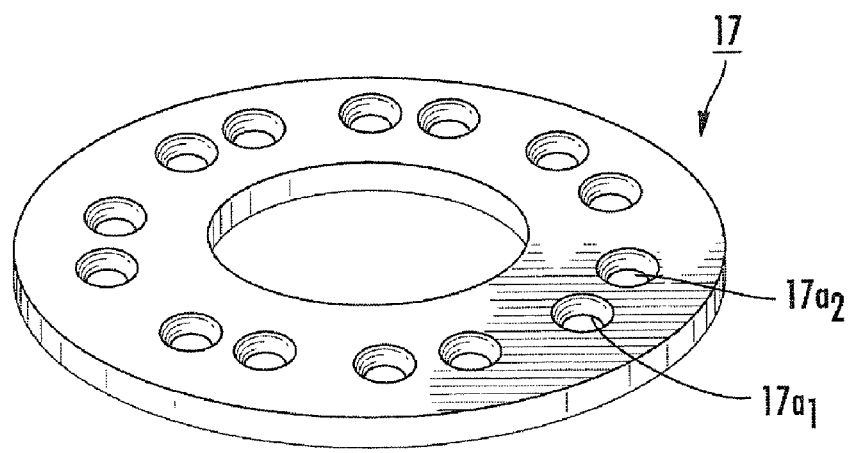
FIGS. 7A-7C are perspective views of alternative blister packages suitable for concurrent dispensing of a plurality of separately held medicaments or dry powders according to embodiments of the present invention.
Figure 7B:
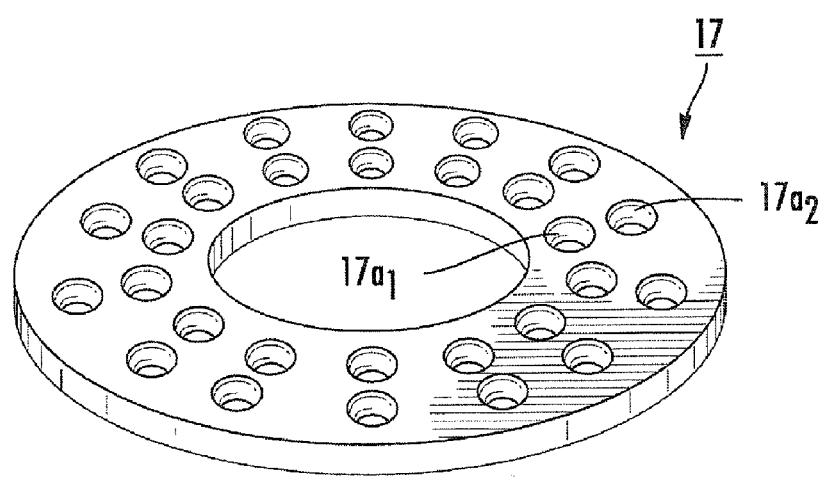
Figure 7C:
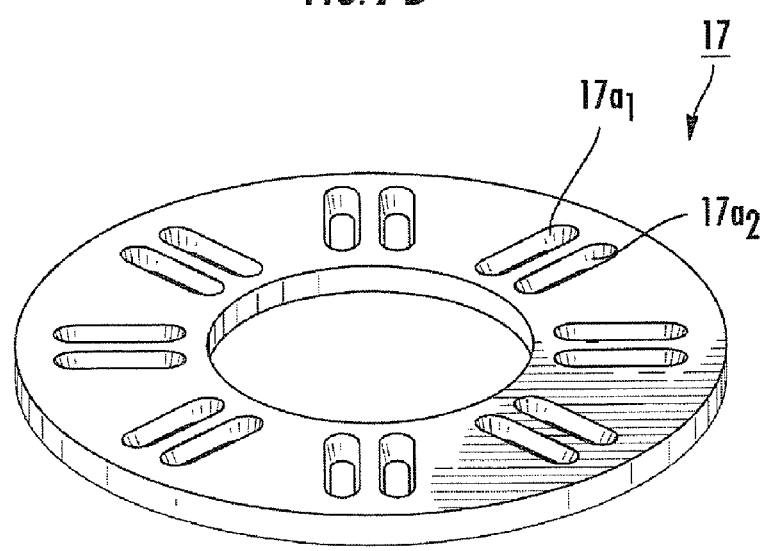

FIGS. 7A-7C illustrate alternative configurations of the intermediate member 17 with closely spaced neighboring intermediate member apertures $17a_1$, $17a_2$ that define a sidewall(s) of corresponding blisters $15b_1$, $15b_2$ (not shown) which can be used to concurrently dispense the dry powder in neighboring blisters for combination therapeutic treatments. The neighboring apertures $17a_1$, $17a_2$ (which may be pairs or sets of three of more apertures) may be spaced closer together on the intermediate member 17 than the non-neighboring apertures. Each adjacent or neighboring blister $15b_1$, $15b_2$ may contain different medicaments and/or dry powders therein that can be concurrently released upon inhalation during operative use. FIG. 7A illustrates side by side, neighboring (adjacent) pairs of apertures $17a_1$, $17a_2$ that form the sidewall(s) of corresponding blisters $15b_1$, $15b_2$ (not shown) that are configured to be jointly dispersed upon inhalation in an inhaler. FIG. 7B illustrates front to back neighboring blister sidewalls $17a_1$, $17a_2$ that can also configured to be jointly dispersed upon inhalation via an inhaler. FIG. 7C illustrates yet another side-by-side configuration with neighboring elongate apertures $17a_1$, $17a_2$. In certain embodiments, the side-by-side aperture/blister configurations may be offset lengthwise (not shown) across the blister package.

Figure 9:
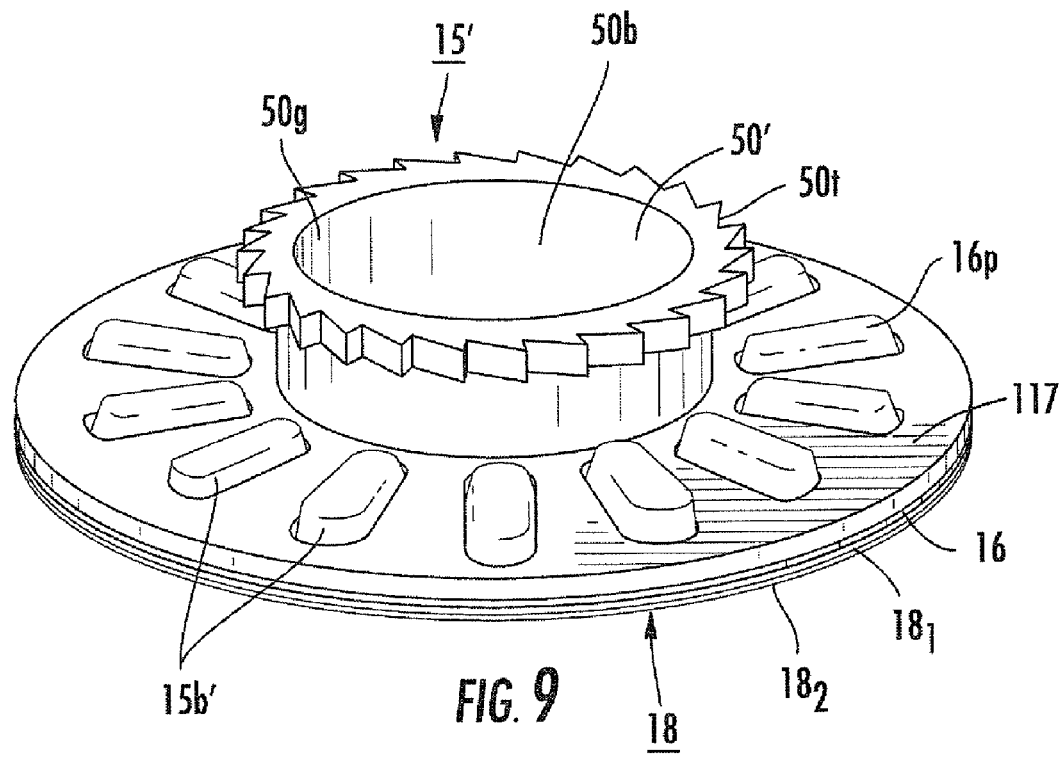
FIG. 9 is a top perspective view of a blister package according to additional embodiments of the present invention.
Figure 10:
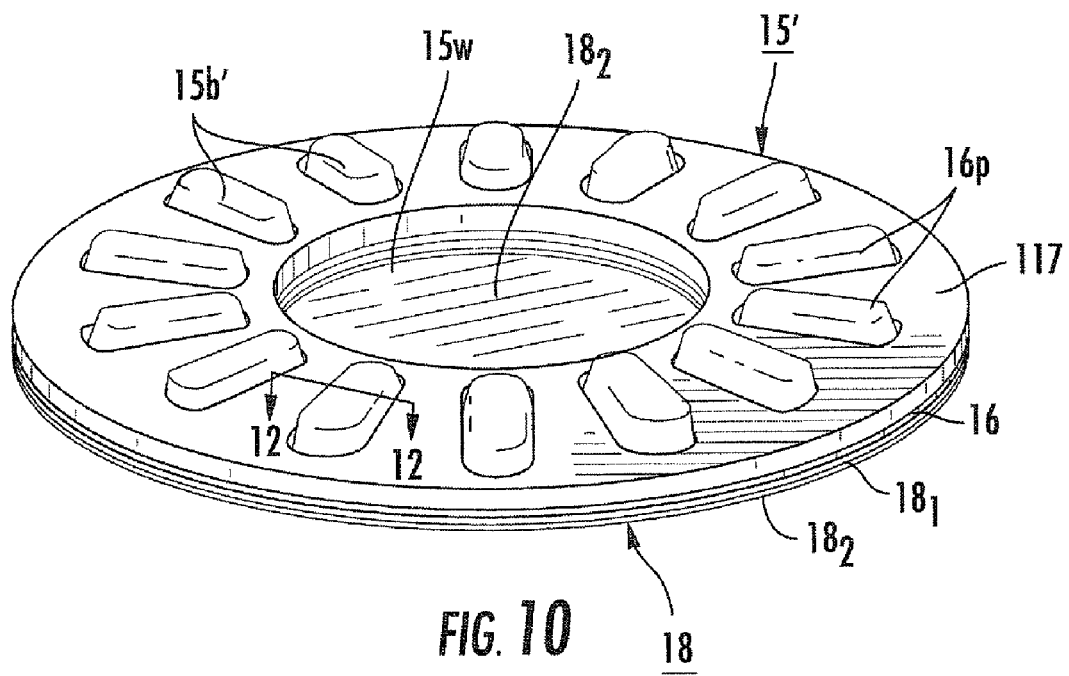
FIG. 10 is a top perspective view of yet another blister package similar to that shown in FIG. 9, but without the gear component, according to embodiments of the present invention.
Figure 11:
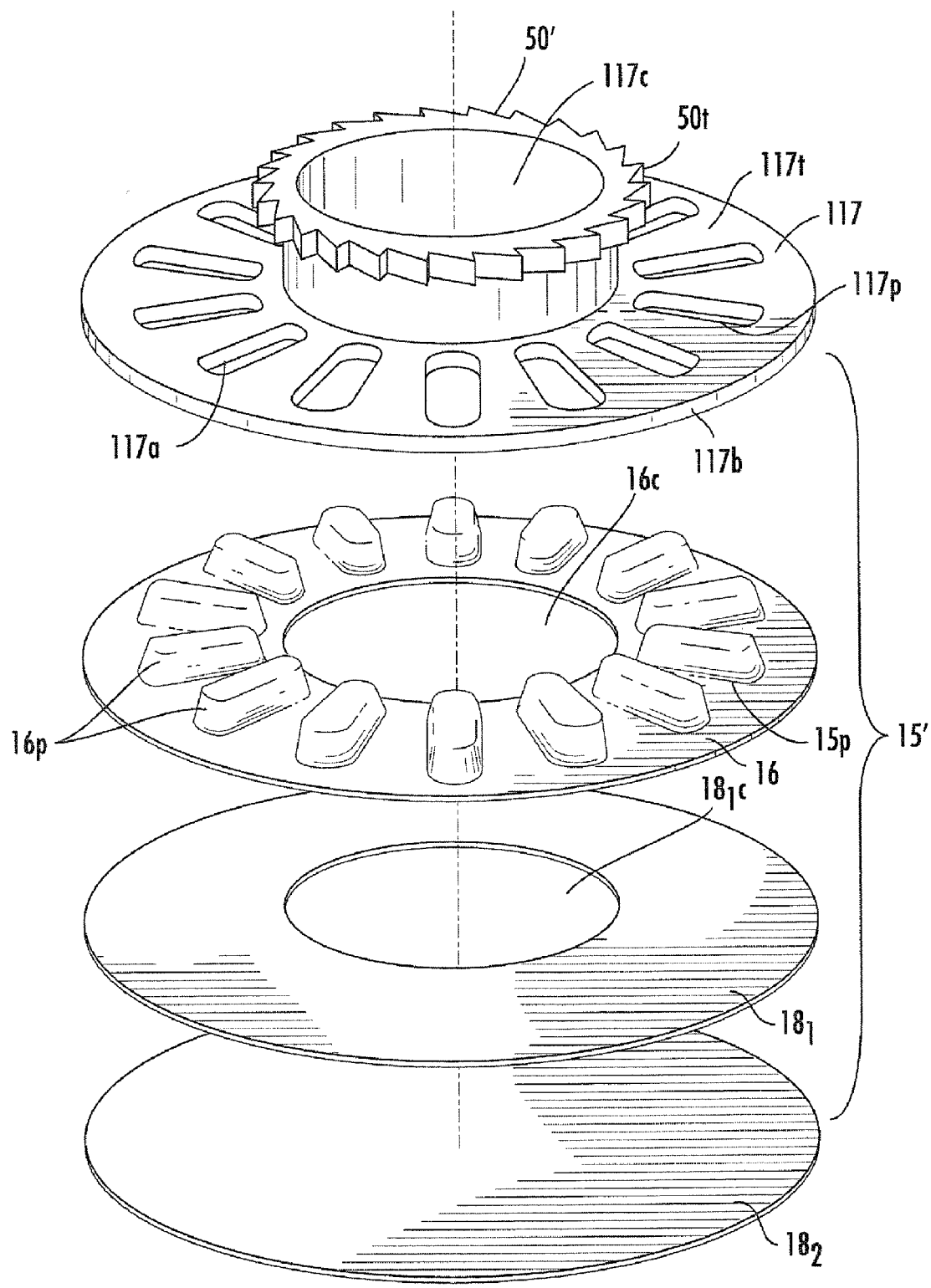
FIG. 11 is an exploded view of components that may be used to form the blister package shown in FIG. 9 or 10 according to embodiments of the present invention.

FIGS. 9-12B illustrate an alternative embodiment of a blister package 15'. As shown, the blister package 15' includes the ceiling 16 that has a body that resides below a frame 117. The frame 117 overlies the ceiling 16 and includes a plurality of apertures 117a that are sized and configured to allow the blister ceiling projections 16p to extend therethrough. The frame 117 can be configured to resist flexure and/or have increased rigidity relative to the floor 18 and/or ceiling 16 of the blister package. The frame 117 can have a thickness that is greater than the combined thickness of the ceiling 16 and floor 18. The frame 117 can have a molded body comprising a polymer material. The frame 117 may be between about 0.25-2 mm thick, and typically between about 0.5-1 mm thick. In certain embodiments, the frame 117 may be substantially rigid. The frame 117 can have a substantially planar top and bottom surface 117t, 117b (FIG. 11).

Figure 12A:
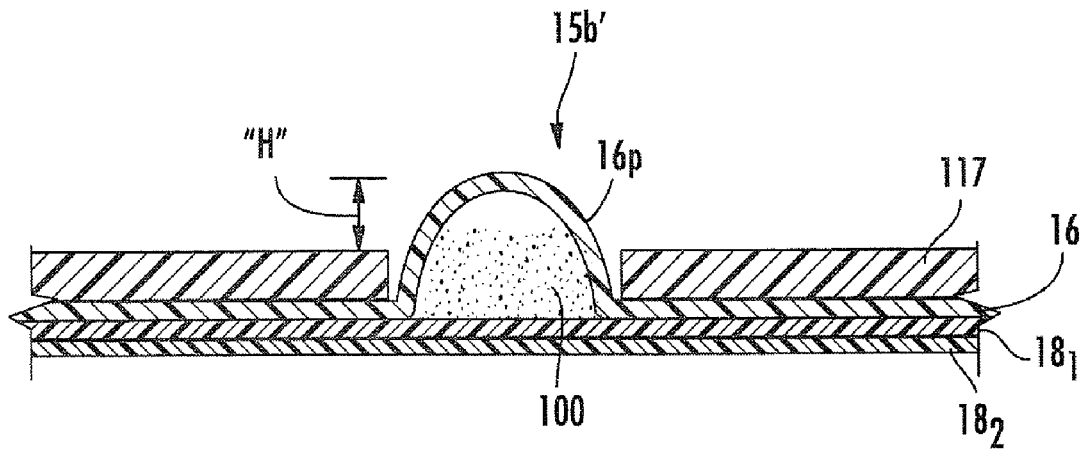
FIGS. 12A and 12B are enlarged partial side section views of a blister package such as those shown along line 12-12 in FIG. 10 illustrating exemplary blister configurations according to embodiments of the present invention.
Figure 12B:
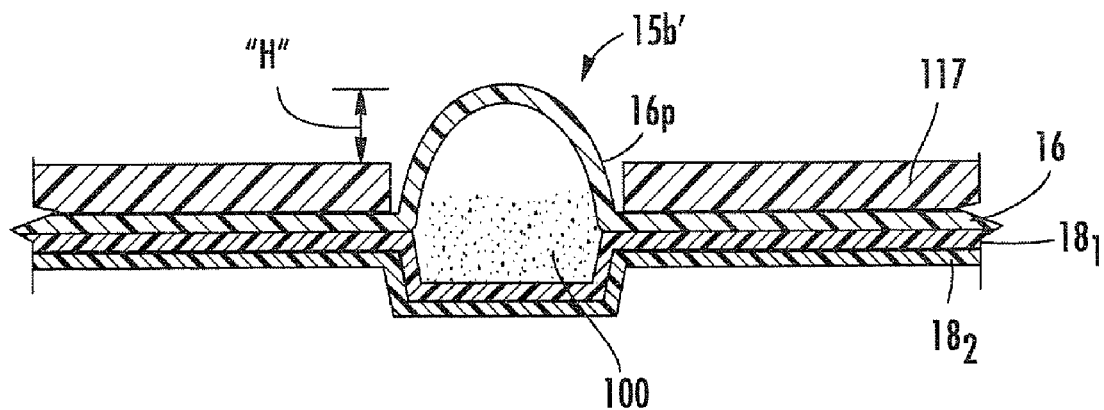

In certain embodiments, the ceiling projections 16p are configured to rise above the top surface 117t of the frame 117 a desired distance. As shown in FIGS. 12A and 12B, the ceiling projection 16p may rise a distance "H" above the frame 117 between about 1-10 mm, typically at least about 2 mm. As shown, the blister 15b is formed by the sealing of the floor 18 with the ceiling 16 (the frame 117 does not form the sidewalls of the blister). The floor 18 of the blister 15 may be recessed as shown in FIG. 12B or substantially planar such as shown in FIG. 12A.

The ceiling 16 and floor 18 can be configured as described above. FIG. 11 illustrates that the floor 18 may include a plurality of flexible layers, shown as two floor layers, $18_1$, $18_2$, as discussed above.

FIG. 9 illustrates that the blister package 15' may include a mounting member 50' thereon. As discussed above, the mounting member 50' can include a gear 50g with gear teeth 50t that engage an indexing mechanism in the inhaler as discussed above. As before, the mounting member 50' may be integrally attached to, formed on, or releasably attached to the frame 117 to form a blister package 15'. In other embodiments, as shown in FIG. 10 the blister package 15' is not required to include a mounting member. The gear 50g can include a bore 50b therein which can be configured to allow access to an exposed surface of the active layer $18_2$. The inhaler may include a pin that engages the bore of the gear to hold the gear and blister package in position and allow the gear 50g to rotate in the inhaler. The blister frame 117 and blister package 15' may be configured as a replaceable modular unit for an inhaler. In particular embodiments, the blister frame 117, the gear 50g and the blister package 15' are a modular unit that is disposable after the blisters have been depleted and the inhaler is configured to allow replacement thereof.

It is noted that other and/or additional mounting structures beyond those shown in the figures may be used to configure the blister package 15 for use in an inhaler. It is also noted that the shape of the blisters 15b is not limited to that shown in the embodiments described herein. In particular embodiments, the blister package 15, 15' may be configured to have a substantially disk-like shape. The blister package 15, 15' can be configured to rotate in the inhaler to advance a respective blister into an indexed or registered inhalation position.

In the embodiment shown in FIG. 11, the frame 117 can include a plurality of frame apertures 117a, each with a perimeter shape 117p. The perimeter shape 117p is sized and configured to allow the projecting ceiling 16p of the blister 15b to extend therethrough. The frame aperture perimeter shape 117p may be configured to substantially correspond to the blister perimeter shape 15p when viewed from the top. Thus, the frame aperture 117a may have a shape and size that is substantially the same as the shape and size of a respective blister 15*b*. The blister 15*b* can have a width and length and the aperture 117*a* can have substantially the same width and length (typically just a bit larger than the width/length of the blister).

In certain embodiments, the blister package 15, 15' can include visible indicia and/or can be configured to engage an inhaler to provide audible alerts to warn a user that he/she is approaching the last of the filled blister inhalant doses on the blister package 15, 15' and/or to indicate that the dose was properly (and/or improperly) inhaled or released from the inhaler device. For example, certain dry powder dose sizes are formulated so that it can be difficult for a user to know whether they have inhaled the medicament (typically the dose is aerosolized and enters the body with little or no taste and/or tactile feel for confirmation). Thus, a sensor can be positioned in communication with a blister 15*b* in a dispensing position in an inhaler and configured to be in communication with a digital signal processor or microcontroller, each held in or on the inhaler and/or the blister package 15, 15'. In operation, the sensor is configured to detect a selected parameter, such as a difference in weight, a density in the exiting aerosol formulation, and the like, to confirm that the dose was released.

In certain embodiments, the blister package 15, 15' can include color-enhanced markings for the last few (such as the last 5) doses. The color-enhanced markings may change from darker (orange to salmon or red) or to completely different colors as the last dose or last few doses approach. Alternatively (or additionally), the multi-dose disposable package 15, 15' may be configured with audible alert features that activate a digital signal processor or microcontroller (not shown) housed in the inhaler to generate a stored audible verbal message or warning (such as "warning, refill needed, only five doses remain") when a desired number of doses have been administered.

In certain embodiments, in position, a forward or leading (cutting) edge portion of a blade can be configured to open (typically cut or slice) at least a portion of the projecting ceiling 16*p* of a blister 15*b*, 15*b*' by traveling generally (typically substantially) parallel to a plane extending horizontally about an upper portion of an underlying blister along a length direction thereof at a position that is less than the height of the blister projection, to slice a major portion of the ceiling in the length direction, forming a gap space to allow the dry powder held in the blister 15*b*, 15*b*' to be dispensed.

Figure 13:
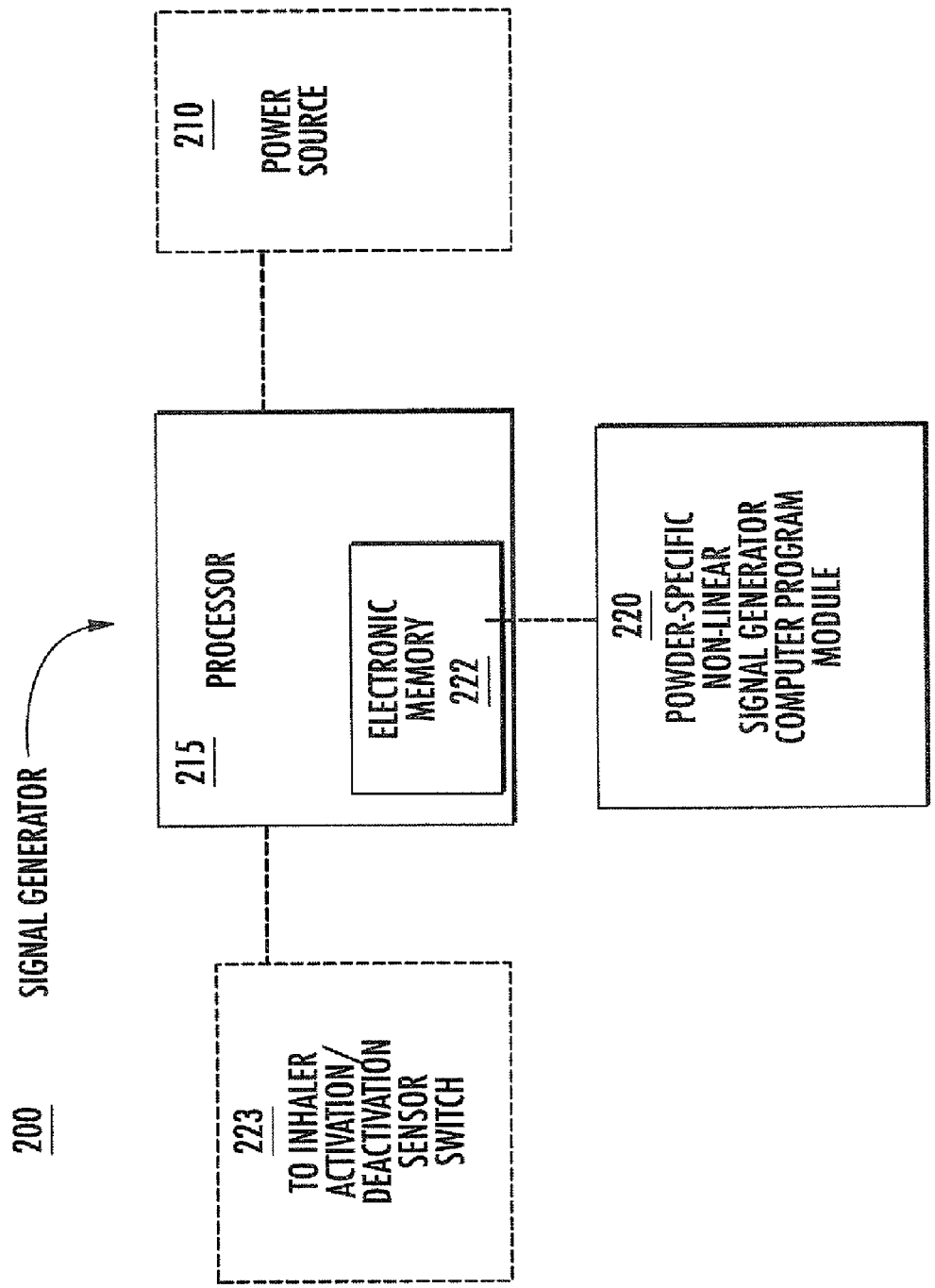
FIG. 13 is a block diagram of a control system with computer program code that may be included on a blister package and/or communicate with an inhaler according to embodiments of the present invention.

FIG. 13 illustrates an example of a signal generator 200 that may be configured to reside in and/or communicate with the blister package 15, 15'. The signal generator can include a processor (such as a digital signal processor) 215 and electronic memory 222. The electronic memory can include, but is not limited to, cache, ROM, PROM, EPROM, EEPROM, flash memory, SRAM, and DRAM.

The signal generator 200 may, in certain embodiments, also include a powder specific non-linear signal generator computer program module 220 that provides the electrical signal characteristics for the drug being dispensed. The module 220 may be programmed into the memory 222. The signal generator 200 may have a sleep or inactive (or off) mode that is turned to an active mode based on inhaler activation via input from a switch or a sensor 223. For example, the signal generator 200 may communicate with a power source 10 such as a battery (typically a miniaturized battery, such as a digital camera or pancake type flat battery) to power the signal generator and transmit the electrical signal to the desired blister 15*b*, 15*b*'. The activation may be carried out automatically based upon input from a sensor and/or activation from an "on" switch.

Examples of an amplitude-modified vibratory signal suitable for vibrating the blister 15*b*, 15*b*' holding the dry powder are described in co-pending U.S. patent application Ser. No. 10/434,009, the contents of which are incorporated by reference as if recited in full herein. The vibratory signal can include a kHz carrier frequency (such as about 5 kHz-50 kHz) modified by low modulating frequency (typically about 10-200 Hz). The frequency of the vibration can be modified to match or correspond to the flow characteristics of the dry powder substance held in the package to attempt to reach a resonant frequency(s) to promote uniform drug dispersion into the body. In some embodiments, a non-linear powder-specific dry powder vibratory energy signal a different powder specific signal for each of the formulations on a blister package or the same for a particular formulation on each package) comprising a plurality of selected frequencies can be generated (corresponding to the particular dry powder being currently dispensed) to output the particular signal corresponding to the dry powder then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

The blister package 15, 15' can include signal-generating circuitry and/or components held thereon or therein which, in operation, are in communication with the blisters 15*b*, 15*b*' (via the conductive pattern 18*p* on the active floor 18$_2$). The signal generating circuitry may be programmed with a plurality of predetermined different input signals, or if the blister package dispenses only a single dry powder, the signal generator may be programmed with a single signal. Appropriate powder-specific signals can be determined experimentally and/or computationally at an OEM or evaluation site and input into the inhalers (via hardware and/or software components including programmable processors). For additional description of signals and operations to determine same, see co-pending and co-assigned U.S. patent application Ser. Nos. 10/434,009, 10/606,678, 10/607,389, and 10/606,676: the contents of these applications are hereby incorporated by reference in their entireties as if recited in full herein.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may be include a plurality (typically at least three) superpositioned modulating frequencies and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

Generally describing some embodiments, in operation, the blister packages 15, 15' are configured to operate with dry powder inhalers. The inhalers can be used for nasal and/or oral (mouth) respiratory delivery. The inhalable dry powder doses can be packaged in multi-dose dry powder drug packages that may include a piezoelectric polymer substrate (such as PVDF) that flexes to deform rapidly and provide mechanical oscillation in an individually selectable signal path on the package. The signal path directs the signal to the region of the drug receptacle or well to cause the well to oscillate in cooperation with a user's inspiratory effort, and, thus, actively direct the dry powder out of the well and up into the exit flow path.

Figure 14:
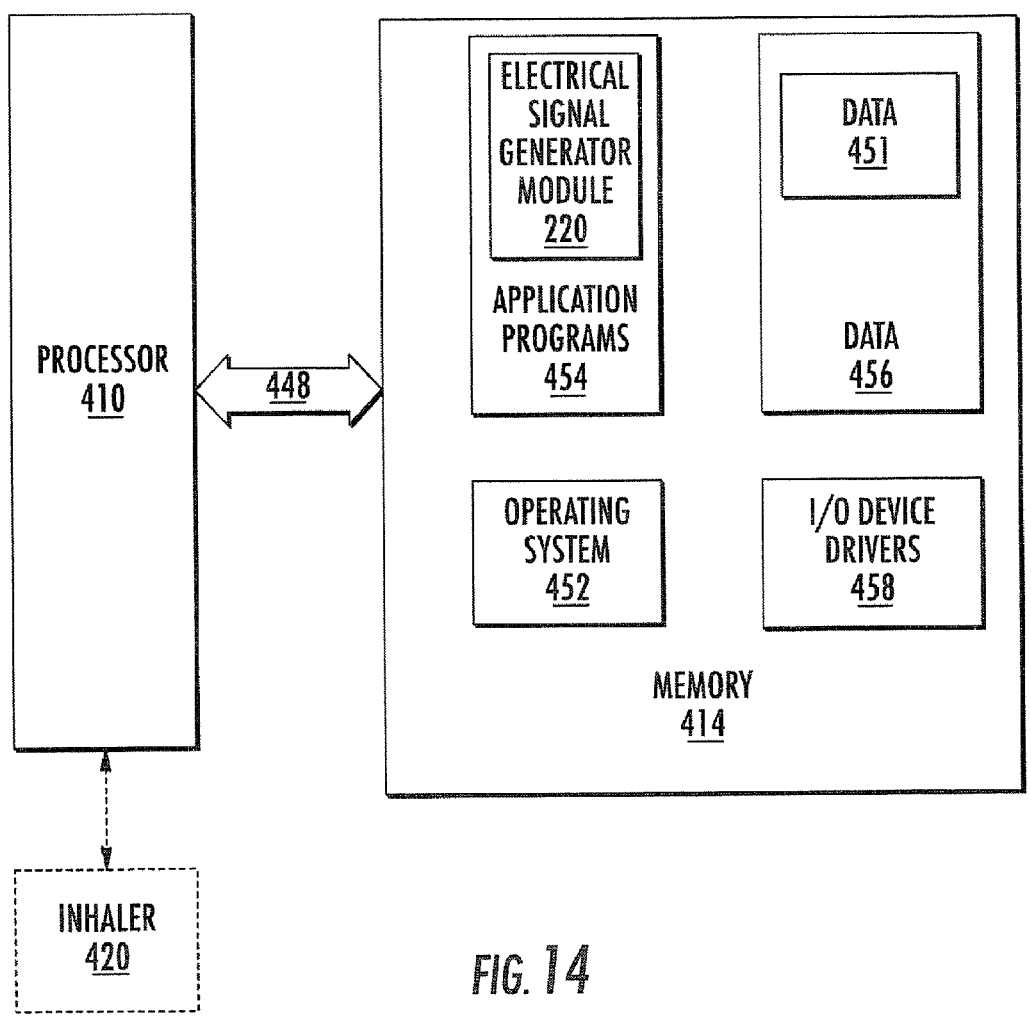
FIG. 14 is a block diagram of a control system and/or data processing system according to embodiments of the present invention.

FIG. 14 is a block diagram of exemplary embodiments of data processing systems that illustrate an example of a computer program product module 220 of FIG. 13 in accordance with embodiments of the present invention. The module 220 may be configured to provide powder specific or other types of electrical signal input signals. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 14, the memory 414 may include several categories of software and data used in the data processing system 405: the operating system 452; the application programs 454; the input/output (I/O) device drivers 458; a powder (specific) signal generator (vibratory) module 220; and the data 456. The data 456 may include: (a) a look-up chart/table data for dry powder signal formulations for plurality of different dry powders 451; (b) in situ acquired measurement data whether to confirm that the dry powder dose was properly (or improperly) dispensed and/or patient inspiratory data, which may be obtained from an operator or stored by the inhaler; (c) and/or timing data that automatically activates the signal and inputs to the blister for dispensing the dry powder based upon a pull operation (pulling the cutting cartridge and/or mouthpiece outward). As will be appreciated by those of skill in the art, the operating system 452 of the inhaler, blister package 15, 15' and/or programmable inputs thereto may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the powder signal generator module 220 being an application program in FIG. 14, as will be appreciated by those of skill in the art, other configurations may also be utilized while still benefiting from the teachings of the present invention. For example, the module 220 may also be incorporated into the operating system 452, the I/O device drivers 458 or other such logical division of the data processing system 405. Thus, the present invention should not be construed as limited to the configuration of FIG. 14, which is intended to encompass any configuration capable of carrying out the operations described herein.

The I/O data port can be used to transfer information between the data processing system 405 and the inhaler dispensing system 420 or another computer system or a network (e.g., the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 14 but is intended to encompass any configuration capable of carrying out the operations described herein.

Figure 15:
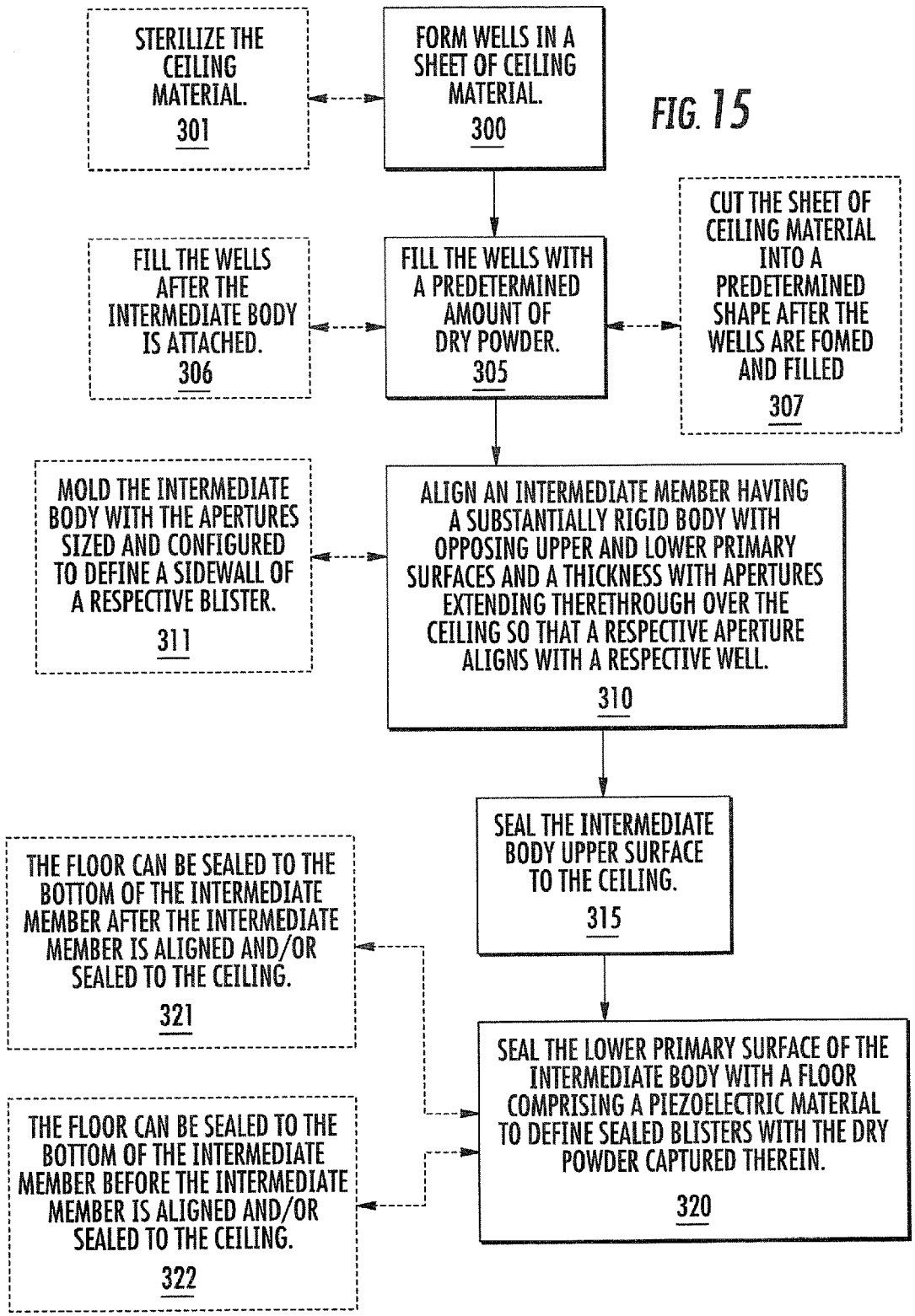
FIG. 15 is a flow chart of operations that can be carried out to fabricate a blister package according to embodiments of the present invention.

FIG. 15 illustrates an example of operations that can be carried out to fabricate a blister package 15 such as that shown in FIGS. 1A, 1B, 5A, 6, and 7A-7C according to embodiments of the present invention. Wells (i.e., projections that are wells when the ceiling is inverted from the configuration shown certain of the figures such as in FIG. 1A) can be formed in the ceiling material (block 300). As noted above, the ceiling material may be a relatively thin laminated structure. The wells can be filled with a predetermined amount of dry powder (block 305). The term "filled" includes providing an amount that is less than the volumetric capacity of the well. The ceiling material may be sterilized prior to (and/or after the wells are formed and/or prior to depositing the dry powder therein) (block 351). An intermediate member having a substantially rigid body with opposing upper and lower primary surfaces and a thickness with apertures extending therethrough can be aligned with the ceiling so that a respective aperture aligns with a respective well (block 310). The intermediate member upper primary surface can be sealed to the ceiling material (block 315) and the opposing primary surface sealed to the floor comprising a piezoelectric material to define sealed blisters with the dry powder captured therein (block 320).

The floor can be sealed to the intermediate member after the intermediate member is aligned with and/or sealed to the ceiling (block 321). Alternatively, the floor can be sealed to the intermediate member before the intermediate member is aligned with and/or sealed to the ceiling (block 322). In addition, the intermediate member can be attached to the ceiling before the dry powder is positioned therein or after the dry powder is held therein. If the latter, the intermediate member is attached to the ceiling while the projections are facing down with the wells holding the dry powder. If the former, the ceiling can be a planar sheet (not requiring projections or wells) as the intermediate member can define a well sized to hold dry powder therein. The sheet of ceiling material can be cut into a predetermined shape after the dry powder is placed in the wells (block 307). If so, a sheet of a first floor layer can be used to seal the intermediate member and the first floor layer sheet cut concurrently with the ceiling material into a desired shape. In other embodiments, the ceiling material and floor can be separately formed into desired shapes prior to attachment. As described above, mounting and/or electrical components can be assembled to the blister package.

Figure 16:
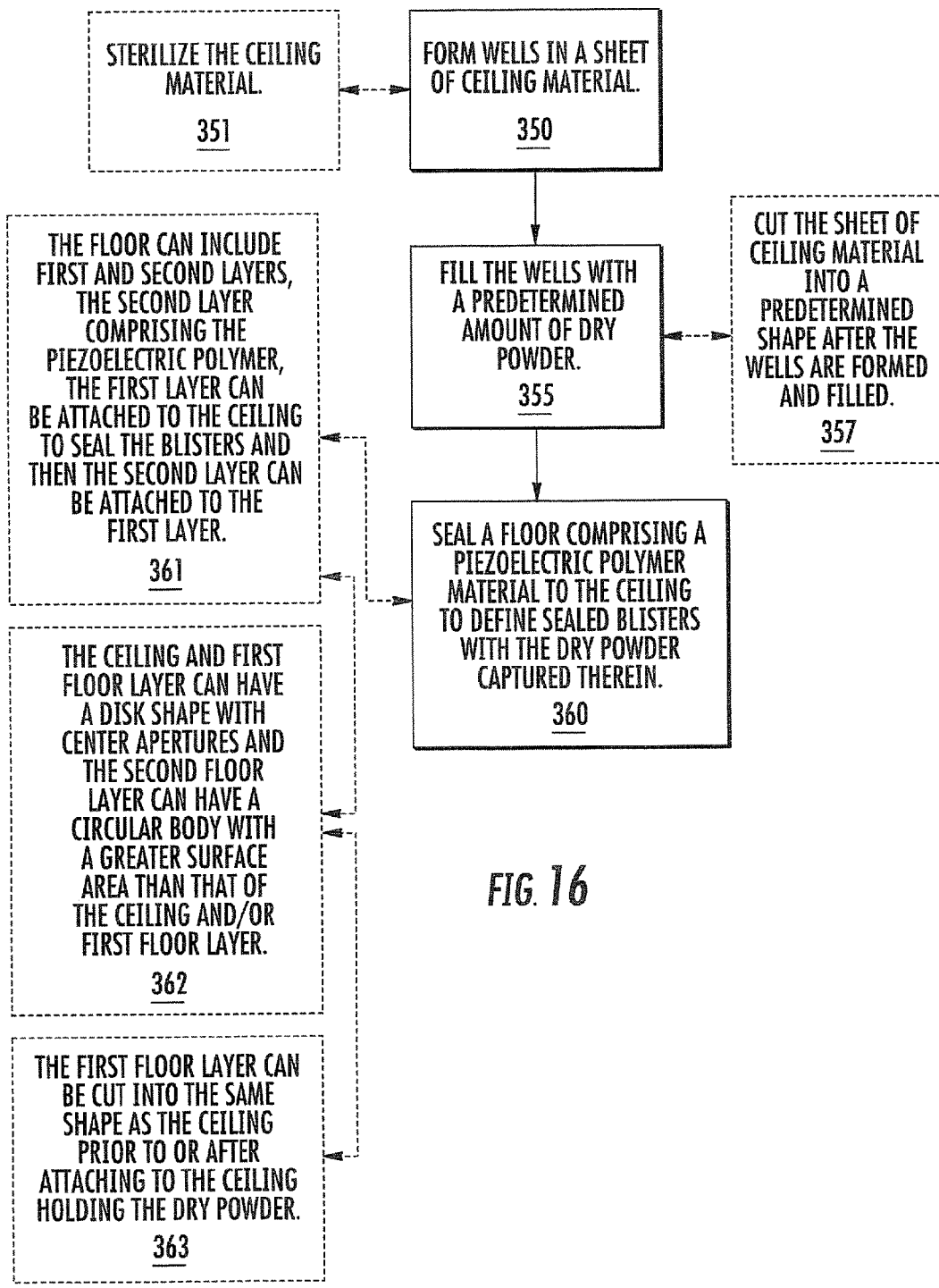
FIG. 16 is a flow chart of operations that can be carried out to fabricate a blister package according to other embodiments of the present invention.

FIG. 16 illustrates operations that can be used to fabricate blister packages 15b' (such as shown in FIGS. 9-12). As before, wells can be formed into the ceiling material (block 350). The wells can be filled with a desired amount of dry powder (block 355). A floor comprising a piezoelectric polymer material can be sealed to the ceiling to define sealed blisters with the dry powder captured therein (block 360). The ceiling (and floor) can be sterilized (block 351).

In certain embodiments, the floor can include first and second layers, the second layer comprising the piezoelectric polymer. The first layer can be a flexible material (i.e., lid stock and/or foil release material) that can be sealed to the ceiling to seal the blisters with the dry powder held therebetween and then the second layer can be attached to the first floor layer (block 361).

As before, the sheet of ceiling material can be cut into a predetermined shape after the dry powder is placed in the wells (block 357). The first floor layer can be cut into substantially the same shape as the ceiling prior to and/or after attaching to the ceiling holding the dry powder (block 363). If the latter, a sheet of the first floor layer can be cut concurrently with the ceiling material into a desired shape. The ceiling and floor layer can have a disk-like shape with center apertures and the second floor layer can have a substantially circular body with a greater surface area than that of the ceiling and or first layer of the floor (block 362). In other embodiments, the ceiling material and floor can be separately formed into desired shapes prior to attachment. As described above, mounting and/or electrical components can be assembled to the blister package.

Figure 17:
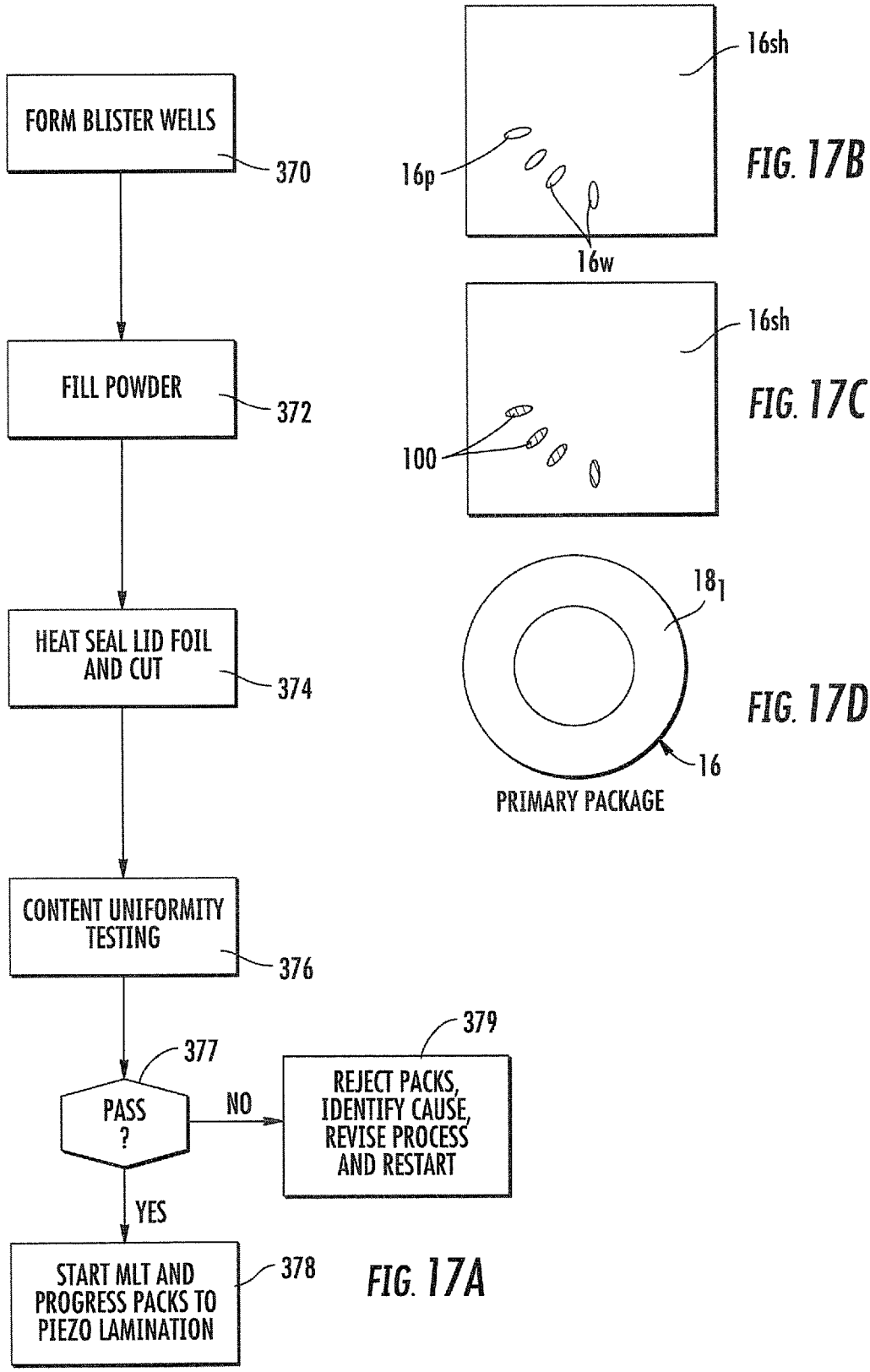
FIG. 17A is a flow chart of operations that can be carried out to fabricate a blister package according to further embodiments of the present invention.
FIGS. 17B-17D illustrate a serial progression of configurations of a blister package during the fabrication operations shown in FIG. 17A.

FIG. 17A illustrates operations that may be used to fabricate a primary blister package to which a piezoelectric material may be subsequently applied according to some embodiments of the present invention. As shown, blister wells can be formed in a ceiling material sheet (block 370). FIG. 17B illustrates a ceiling sheet 16sh with the sheet oriented with the projections 16p down to define the wells 16w. As shown in FIG. 17A, the wells 16w can be filled with dry powder (block 372). FIG. 17C illustrates the dry powder 100 in the wells 16w. The first floor layer of the floor, which can comprise a foil, is heat sealed to the ceiling and the sealed structure cut into a desired shape (block 374) and FIG. 17D. The blister package can undergo a content uniformity assessment or inspection (block 376). If the blister package passes, the blister package can proceed to piezoelectric lamination operation (block 378). If the blister package fails, the package is rejected, the cause may be identified so that the process can be adjusted and/or corrective action taken as needed (block 379).

Figure 18:
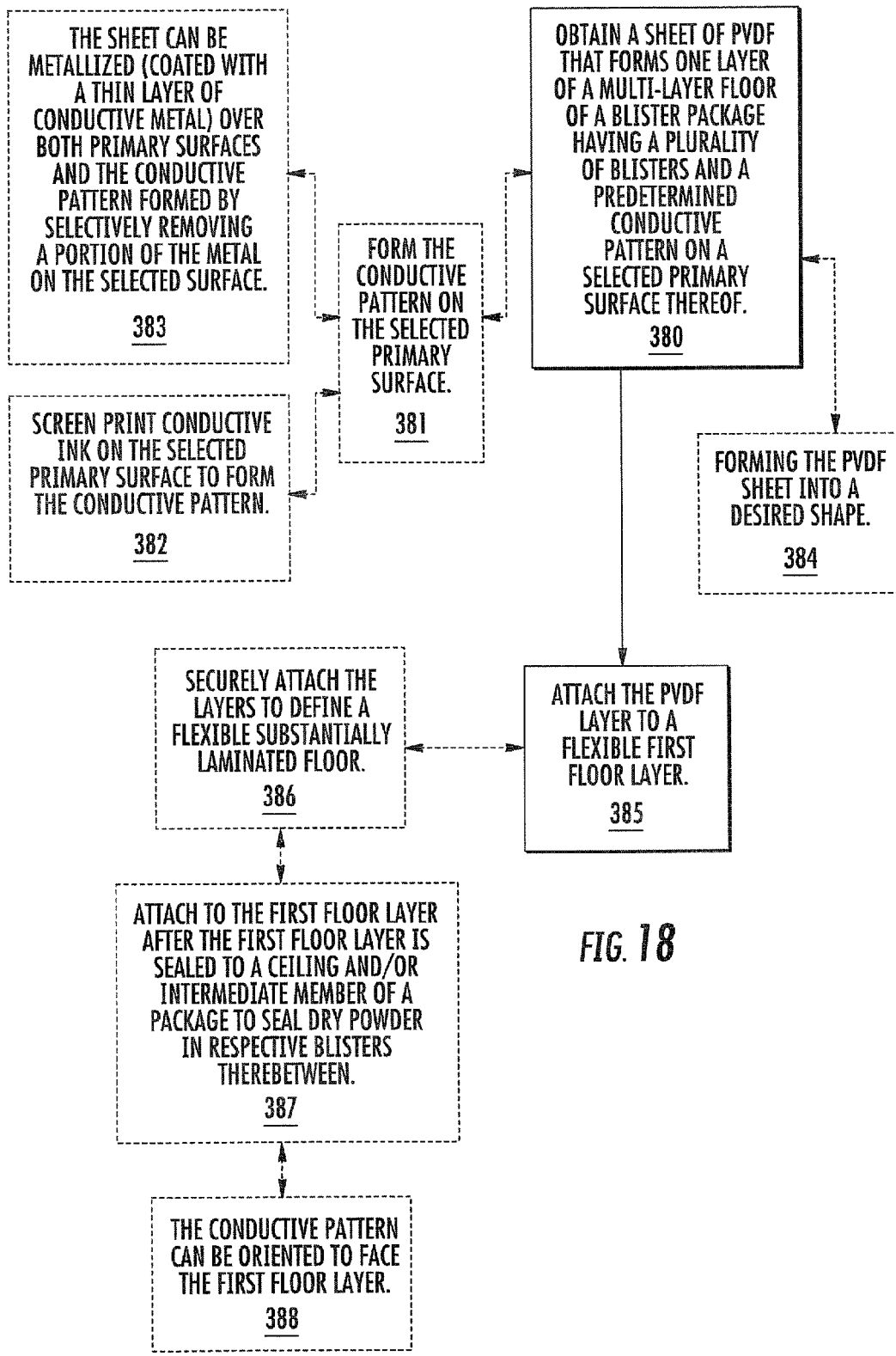
FIG. 18 is a flow chart of operations that can be used to form a floor of a blister package according to embodiments of the present invention.

FIG. 18 illustrates exemplary operations for providing a suitable piezoelectric or active floor layer. A sheet of PVDF can be obtained with a predetermined conductive pattern on a selected primary surface thereof (block 380). The predetermined conductive pattern can be formed on the selected primary surface (block 381) or pre-configured thereon. The PVDF layer can be attached to a flexible first floor layer (block 385). As noted above, the PVDF layer can be applied to the first layer after the first layer is sealed to the ceiling (or intermediate member) or before.

In certain embodiments, the PVDF sheet can be metallized (coated, formed, or otherwise deposited with a thin metal layer) that can substantially cover both primary surfaces (typically not the minor surfaces) and the conductive pattern formed by selectively removing a portion of the metal on the selected primary surface (block 383). In other embodiments, the conductive pattern can be screen printed on the PVDF sheet (block 382). However, as noted above other conductive pattern formation techniques may also be used.

The PVDF sheet can be formed into a desired shape (block 384). The shape can be formed prior to or after the formation of the conductive pattern. The shape of the PVDF floor layer can be substantially circular (and planar). The flexible floor layers can be securely attached to define a flexible substantially laminated floor (block 386). The first floor layer can be attached after the first floor layer is sealed to the ceiling and/or intermediate member (block 387). The PVDF layer may be adhesively attached, heat and/or pressure bonded or otherwise attached. The conductive pattern may be oriented to face the first floor layer (block 388).

FIG. 19A illustrates operations to form a multi-layer flexible floor with PVDF according to some particular embodiments of the present invention. As shown, a disk or other desired shape can be cut from PVDF material that has been metallized (block 390). The metallization can be selectively removed from one primary surface (block 391). FIG. 19B illustrates the two opposing primary surfaces of the active floor layer $18_2$, one having metallization over substantially its entire surface and the other having the predetermined conductive pattern formed by the selective removal. A plurality of the shaped floor pieces can be positioned on a common pressure sensitive adhesive (PSA) carrier or transfer liner 188 as shown in FIG. 19C. PSA can be applied to one of the primary surfaces of the shaped floor layer $18_2$ members and compressed to transfer PSA to the contact surface (block 392). The floor members $18_2$ can be further cut or formed to a desired (primary) package size (block 393). FIG. 19D illustrates the floor layers $18_2$ with a backing liner of surface adhesive $18_2$s thereon. The floor layers $18_2$ can be (electrically) tested for signal integrity (such as circuit transmission paths and/or noise) (block 394). The testing can be carried out prior to applying the adhesive or without removing from the common carrier liner. If acceptable, the floor $18_2$ can be separated from the liner, a floor member $18_2$ can be aligned with a blister package 15, 15' and pressure applied to attach the floor layer $18_2$ thereto (block 395). If the floor layer $18_2$ fails the test, the floor $18_2$ is rejected (block 396) (and discarded or repaired). FIG. 19E illustrates a finished package 15, 15' with the floor layer $18_2$ attached to the bottom of the primary package with the sealed blisters.

Certain operations may be automated and/or carried out using computer programs and automated equipment.

The flowcharts and block diagrams of certain of the figures herein illustrate the architecture, functionality, and operation of possible implementations of dry powder-specific dispensing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the powder specific vibration energy signals are non-linear and the inhaler can include computer program code that automatically selectively adjusts the output of the vibration energy signal based on the identified dry powder being dispensed. The vibration energy output signals for the dry powders being dispensed can be based on data obtained from a fractal mass flow analysis or other suitable analysis of the dry powder being administered to the user. The inhaler may be particularly suited to dispense low-density dry powder.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A multi-dose blister package adapted for use in an inhaler, comprising:
   a substantially rigid frame member configured to resist flexure having a plurality of spaced apart apertures;
   a ceiling having a corresponding plurality of spaced apart projections, the ceiling disposed under the frame member and oriented relative to the frame member so that a respective ceiling projection extends through and rises above a respective frame aperture;
   a flexible floor underlying and attached to the ceiling, wherein the ceiling and floor are configured to define a plurality of spaced apart scaled blisters therebetween, wherein the floor comprises a flexible piezoelectric material; and
   a quantity of dry powder held in each sealed blister;
   wherein the frame member has a thickness that is at least five times greater than that of the ceiling and floor, and wherein, the blister package is configured so that the blister is opened from the ceiling while the floor remains intact.

2. A multi-dose blister package according to claim 1, wherein the frame member has a substantially planar body, and wherein the frame member has sufficient rigidity to remain substantially planar daring operation, wherein the ceiling is a substantially continuous layer that is sized and configured to extend over all of the blisters under the frame member with the projections aligned to reside in the frame member apertures.

3. A multi-dose blister package according to claim 1, wherein the floor comprises substantially laminated first and second flexible layers, with at least one of the first and second layers comprising the piezoelectric material and wherein, in operation, the piezoelectric material underlying a target blister is configured to repeatedly flex generally upward and downward upon receipt of an electrical input.

4. A multi-dose blister package according to claim 1, further comprising a bolus quantity of dry powder disposed in respective blisters.

5. A multi-dose blister package according to claim 4, wherein the package is adapted to be releaseably inserted into an inhaler and disposable after the dry powder in the blisters has been depleted.

6. A multi-dose blister package according to claim 4, wherein the dry powder is a low-density clay powder.

7. A multi-dose blister package according to claim 1, wherein the floor comprises first and second flexible layers of different materials, a selected one of the layers comprising a piezoelectric film.

8. A multi-dose blister package according to claim 7, wherein the floor second layer comprises the piezoelectric film material and is attached to a bottom of the floor first layer, the floor second layer further comprising a predetermined conductive pattern disposed over a first primary surface and a conductive material disposed over at least a portion of an opposing second primary surface.

9. A multi-dose blister package according to claim 8, wherein the conductive material on the second primary surface of the second layer comprises a metallized coating disposed to cover substantially all of the second primary surface.

10. A multi-dose blister package according to claim 8, wherein the predetermined conductive pattern on the second layer comprises a plurality of spaced apart conductive regions, each region sized and configured to be substantially coextensive with a bottom portion of a respective blister.

11. A multi-dose blister package according to claim 10, wherein the predetermined conductive pattern further comprises at least one signal trace extending away from each region.

12. A multi-dose blister package according to claim 11, wherein the signal trace for each blister travels toward a respective conductive contact zone on the first primary surface of the second layer.

13. A multi-dose blister package according to claim 8, wherein the first floor layer comprises foil.

14. A multi-dose blister package according to claim 13, wherein the second layer of the floor is defined by a PVDF film.

15. A multi-dose blister package according to claim 8, wherein the second layer is a PVDF layer that has a surface area that is about the same as that of the first floor layer.

16. A multi-dose blister package according to claim 8, wherein the second layer is a PVDF layer that has a surface area that is less than that of the first floor layer.

17. A multi-dose blister package according to claim 16, wherein the second layer has a shape that generally corresponds to the shape of the predetermined conductive pattern.

18. A multi-dose blister package according to claim 8, wherein, in operation, the piezoelectric polymer is electrically activated to vibrate a desired blister.

19. A multi-dose blister package according to claim 18, wherein the ceiling is a foil-containing ceiling having sufficient structural rigidity to be formed into and retain the ceiling projection shapes.

20. A multi-dose blister package according to claim 7, wherein the ceiling, frame member, and first layer of the floor have a circular shape with substantially aligned center apertures that expose a portion of an upper surface of the second layer.

21. A multi-dose blister package according to claim 20, further comprising a rotatable gear having circumferentially spaced apart gear teeth, the gear disposed in a window defined by the aligned center apertures and mounted to the frame member so that the blister package rotates with the gear.

22. A multi-dose blister package according to claim 1, wherein the package is configured with blister pairs of sealed blisters that comprise a different dry powder held therein.

23. A multi-dose blister package according to claim 22, wherein the blister pairs are sized and configured to, in operation and in position in an inhaler, release their dry powders in combination substantially concurrently to a user upon inhalation.

24. A multi-dose blister package according to claim 22, wherein the package is configured with a plurality of blister pairs that are circumferentially spaced apart, wherein each blister in a respective blister pair resides closely spaced to each other at a first distance and each blister in the respective blister pair is spaced apart from the next neighboring blister of a different blister pair a second distance that is greater than the first distance.

25. A multi-dose blister package according to claim 1, wherein the ceiling comprises foil.

26. A multi-dose blister package according to claim 1, wherein the frame member comprises a molded polymer body.

27. A multi-dose blister package according to claim 1, wherein the frame member is a substantially flat circular shape with a center aperture and comprises a polymer material.

28. A multi-dose blister package according to claim 1, wherein the frame member is releaseably attached to the ceiling.

29. A multi-dose blister package according to claim 1, wherein the frame member is non-releasably attached to the ceiling.

30. A multi-dose blister package according to claim 1, wherein the ceiling is configured with a selected formable material having sufficient thickness and structural rigidity to be able to retain the projecting ceiling shapes.

31. A multi-dose blister package according to claim 1, wherein the blisters have a perimeter shape when viewed from the top, wherein the frame member apertures have substantially the same blister perimeter shape when viewed from the top, and wherein a respective frame member aperture surrounds a corresponding blister perimeter shape.

32. A multi-dose blister package according to claim 31, wherein the blister perimeter shape is substantially circular when viewed from the top.

33. A multi-dose blister package according to claim 31, wherein the blister has an elongate perimeter shape.

34. A multi-dose blister package according to claim 1, further comprising a power source and an input signal generating circuit that is configured to provide electrical input to selectively flex the floor of a target blister held in a dispensing location in the inhaler, responsive to the electrical input.

35. A multi-dose blister package according to claim 34, further comprising a controller comprising computer readable program code that is in communication with the input signal generating circuit and is configured with a predetermined non-linear vibration input signal selected to represent a priori flow characteristic frequencies of the dry powder formulation held in the blister.

36. A multi-dose blister package according to claim 1, wherein the substantially rigid frame member is a molded polymer with a thickness that is at least ten times greater than that of the ceiling or floor.

37. A method for making a multi-dose blister package adapted for use in an inhaler, comprising:
 providing a substantially rigid frame member configured to resist flexure having a plurality of spaced apart apertures;
 forming a plurality of spaced apart wells in a ceiling that, in position on a sealed blister package, define projections;
 positioning the ceiling above the frame and aligned therewith so that a respective ceiling well extends through and falls below a respective frame aperture;
 positioning a quantity of dry powder in the ceiling wells; and
 sealing a flexible floor comprising a flexible piezoelectric material to the ceiling to define a plurality of spaced apart sealed blisters therebetween, wherein in operation the floor remains intact,
 wherein the frame member has a thickness that is at least five times greater than that of the ceiling and floor.

38. A method according to claim 37, wherein the frame member has a substantially planar body with sufficient rigidity to remain substantially planar during operation, wherein the ceiling is a substantially continuous layer that is sized and configured to extend over all of the blisters under the frame member, further comprising inverting the sealed blister package after the sealing step so that, in operative position, the frame member defines a top surface with the ceiling underlying the frame member with the ceiling projections extending above the frame member through the frame member apertures.

39. A method according to claim 37, wherein the floor comprises a piezoelectric film.

40. A method according to claim 37, further comprising attaching first and second flexible floor layers, at least one of the first and second layers comprising the flexible piezoelectric material, the first and second floor layers configured, in operation, so that the piezoelectric material is configured to repeatedly flex generally upward and downward under a blister upon receipt of an electrical input.

41. A method according to claim 40, wherein the floor second layer comprises the piezoelectric material, the method further comprising forming a predetermined conductive pattern on a selected primary surface of the piezoelectric material before attaching the first and second floor layers together.

42. A method according to claim 41, further comprising metallizing the opposing primary surface of the second floor.

43. A method according to claim 41, wherein the predetermined conductive pattern on the second layer comprises a plurality of spaced apart conductive regions, each region sized and configured to be substantially coextensive with a bottom portion of a respective blister.

44. A method according to claim 43, wherein the predetermined conductive pattern is formed to comprise at least one signal trace extending away from each region.

45. A method according to claim 44, wherein the signal trace for each blister is formed to travel toward a respective conductive contact zone on a primary surface of the second layer.

46. A method according to claim 45, wherein the signal trace for each blister is formed to extend toward a different contact zone.

47. A method according to claim 45, wherein selected pairs of blisters have traces that travel toward a common contact zone that is spatially separate from the other contact zones for the other blisters.

48. A method according to claim 40, wherein the ceiling, frame member, and first layer of the floor have a circular shape with center apertures, the method further comprising substantially aligning the center apertures to expose a portion of an upper surface of the second layer.

49. A method according to claim 40, wherein the floor second layer comprises a piezoelectric film, wherein the sealing step comprises:
attaching the first floor layer to the ceiling to concurrently seal the blisters with the dry powder captured therein; and then
attaching the second floor layer to the first floor layer.

50. A method according to claim 49, further comprising cutting the ceiling and first floor layer into a desired shape after the sealing step before the second floor layer is attached to the first floor layer.

51. A method according to claim 49, further comprising inverting the sealed blister package after the first attaching step so that, in operative position, the frame member defines a top surface with the ceiling underlying the frame member with the ceiling projections extending above the frame member through the frame member apertures.

52. A method according to claim 49, further comprising inverting the sealed blister package after the first and second attaching steps are complete so that, in operative position, the frame member defines a top surface with the ceiling underlying the frame member with the ceiling projections extending above the frame member through the frame member apertures.

53. A method according to claim 49, further comprising testing the second floor layer and/or blister package for electrical integrity of the piezoelectric material and/or predetermined conductive pattern.

54. A method according to claim 37, wherein the floor comprises first and second flexible layers of different materials, a selected one of the layers comprising a piezoelectric film.

55. A method according to claim 37, further comprising forming pairs of sealed blisters so that each blister in a respective blister pair resides closely spaced to each other at a first distance and each blister in the respective blister pair is spaced apart from the next neighboring blister of a different blister pair a second distance that is greater than the first distance, and wherein the positioning step comprises placing a different dry powder in the blisters of each blister pair.

* * * * *

UNITED STATES PATENT AND TRADEMARK OFFICE
CERTIFICATE OF CORRECTION

PATENT NO. : 7,377,277 B2  Page 1 of 1
APPLICATION NO. : 10/970549
DATED : May 27, 2008
INVENTOR(S) : Hickey et al.

It is certified that error appears in the above-identified patent and that said Letters Patent is hereby corrected as shown below:

Column 21, Claim 1, Line 51:   Please correct "scaled"
                                To read -- sealed --

Column 21, Claim 2, Line 63:   Please correct "daring"
                                To read -- during --

Signed and Sealed this

Fifth Day of August, 2008

JON W. DUDAS
*Director of the United States Patent and Trademark Office*